United States Patent [19]
Gelder

[11] Patent Number: 6,043,347
[45] Date of Patent: Mar. 28, 2000

[54] COMPOSITIONS AND METHODS FOR TREATING VIRAL INFECTIONS

[75] Inventor: Frank B. Gelder, Shreveport, La.

[73] Assignee: Probe International Inc., Shreveport LA

[21] Appl. No.: 08/948,782

[22] Filed: Oct. 10, 1997

Related U.S. Application Data

[60] Provisional application No. 60/028,194, Oct. 10, 1996.

[51] Int. Cl.[7] .............................. C07K 16/00; C12Q 1/70; A61K 38/00
[52] U.S. Cl. ........................ 530/388.35; 435/5; 530/324; 530/325; 530/326; 530/389.4
[58] Field of Search .............................. 530/388.35, 324, 530/325, 326, 389.4; 435/5

[56] References Cited

U.S. PATENT DOCUMENTS 5,156,949  10/1992  Luciw et al. ................. 435/5

OTHER PUBLICATIONS

Norrby et al., Comparison of Linear Antigenic Sites in the Envelope Proteins of Human Immunodeficiency Virus (HIV) Type 2 and Type 1, AIDS Res. Hum. Retroviruses 7: 279–285, see 282, col. 1, paragraph 4, 1991.

Kent et al., Identification of Two Neutralizing and 8 Non--Neutralizing Epitopes on Simian Immunodeficiency Virus Envelope Using Monoclonal Antibodies, AIDS Res. Hum. Retroviruses 8:1147–1151, see Abstract, last sentence, 1992.

Kusk et al., AIDS Res. Human Retro., 1992, vol. 8, No. 10, pp. 1789–1794.

Laman et al., AIDS Res. Human Retro., 1993, vol. 9, No. 7, pp. 605–612.

Chequer Bou–Habib et al., Journal of Virology, Sep. 1994, vol. 68, No. 9, pp. 6006–6013.

McKnight et al., Journal of Virology, Jul. 1996, vol. 70, No. 7, pp. 4598–4606.

Ehrhard et al., Biochemistry, 1996, vol. 35, No. 28, pp. 9097–9105.

Bou et al., AIDSLINE, AN 95:13321, 1995.

Shi et al., AIDSLINE, AN 93:10991, 1993.

*Primary Examiner*—Hankyel Park
*Attorney, Agent, or Firm*—Rothwell, Figg, Ernst & Kurz

[57] ABSTRACT

Methods and compositions for treatment, diagnosis, and prevention of a virus comprise administering to a patient antibodies which react with regions of viral proteins and result in neutralization of infectivity and inactivation of functionally essential events in the life cycle of the virus. The antibodies recognize viral epitopes which fail to elicit an immune response in man when encountered through infection or naturally through the environment. In a preferred embodiment, the invention provides compositions and methods useful in the treatment and diagnosis of human immunodeficiency virus (HIV) infections.

28 Claims, No Drawings

COMPOSITIONS AND METHODS FOR TREATING VIRAL INFECTIONS

This application is a continuation of a provisional application 60/028,194 filed on Oct. 10, 1996.

TECHNICAL FIELD

The present invention relates generally to the treatment and prevention of viral infections. In particular, the invention provides compositions and methods for the production of antibodies and peptides useful in the treatment and diagnosis of human immunodeficiency virus (HIV) infections.

BACKGROUND OF THE INVENTION

The diagnosis, treatment and prevention of viral infections is a primary focus of many medical researchers. Although compositions and methods of diagnosing, treating and vaccinating against a number of viral infections are known, there are still a number of viruses which are difficult to detect in man and for which no effective methods of treatment or vaccination against are known. Of these, one of the most significant, of course, is HIV.

The infectious agent responsible for acquired immunodeficiency syndrome (AIDS) and its prodromal phases, AIDS-related complex (ARC) and lymphadenopathy syndrome (LAS), is a lymphotrophic retrovirus termed LAV, HTLV-III, ARV, and recently HIV as recommended by the International Committee on Taxonomy of Viruses (Ref 299). Nomenclature herein employs these recommendations to designated viruses associated with AIDS and the strains thereof. Historic references to strains, which include LAV and ARV-2, are now named HIV1 LAI and HIV1$_{SF2}$, respectively.

As the spread of HIV reaches pandemic proportions, the treatment of infected individuals and prevention of the transmission to uninfected individuals at risk of exposure is of paramount concern. A variety of therapeutic strategies have targeted different stages in the life cycle of the virus and are outlined in Mitsuya and Broder, 1987, *Nature* 325:773. One approach involves the use of antibodies which bind to the virus and inhibit viral replication, either by interfering with viral entry into host cells or by some other mechanism. Once the viral component(s) susceptible to antibody intervention are identified, it has been hoped that antibody reactivity sufficient to neutralize the infectivity of the virus could be generated and administered to HIV-infected patients in the form of immune globulins or purified antibodies and that this passive immunization procedure would alter or reverse progression of HIV infection. In addition, it has been hoped that the vaccination of non-infected individuals with selected epitopes modified to enhance MHC interactions would provide protection from subsequent infection following exposure to HIV.

The envelope glycoproteins of most retroviruses are thought to react with receptor molecules on the surface of susceptible cells, thereby determining the virus' infectivity for certain hosts. Antibodies that bind to these envelope glycoproteins may block the interaction of the virus with the cell receptors, neutralizing the infectivity of the virus. See generally, *The Molecular Biology of Tumor Viruses*, 534 (J. Tooze, ed., 1973); and *RNA Tumor Viruses*, 226, 236 (R. Weiss et al., eds., 1982); Gonzalez-Scarano et al., 1982, *Virology* 120:42 (La Crosse Virus); Matsuno and Inouye, 1983, *Infect. Immun.* 39:155 (Neonatal Calf Diarrhea Virus); and Mathews et al., 1982, *J. Immunol.*, 129:2763 (Encephalomyelitis Virus). To date, therapeutic strategies directed at eliciting protective immune responses in man by vaccination with HIV proteins/peptides have failed. In addition, neither high titer neutralizing antibodies recovered from HIV-infected patients nor monoclonal antibodies produced in mice have succeeded in altering the progression of HIV infection to AIDS and death. There is a need in the art to identify alternate immunological targets on HIV which will elicit immune responses that will modify the course of HIV infection.

The general structure of HIV is that of a ribonucleoprotein core surrounded by a lipid-containing envelope which the virus acquires during the course of budding from the membrane of the infected host cell. Embedded within the envelope and projecting outward are the viral encoded glycoproteins. The envelope glycoproteins of HIV are initially synthesized in the infected cell as a precursor molecule of 150,000–160,000 Daltons (gp 160), which is then processed in the cell into an N-terminal fragment of 110,000–120,000 Daltons (gp 120) to generate the external glycoprotein, and a C-terminal fragment of 41,000–46,000 Daltons (gp 41), which is the transmembrane envelope glycoprotein.

For the reasons discussed above, the gp 120 glycoprotein of HIV has been the object of much investigation as a potential target for interrupting the virus' life cycle. Sera from HIV-infected individuals have been shown to neutralize HIV in vitro, and antibodies that bind to purified gp 120 are present in these sera, (Robert-Guroff et al., 1985, *Nature* 316:72; Weiss et al., 1985, *Nature* 316:69; and Mathews et al., 1986, *Proc. Natl. Acad. Sci. U.S.A.*, 83:9709). Purified and recombinant gp 120 stimulated the production of neutralizing serum antibodies when used to immunize animals (Robey et al., 1986, *Proc. Natl. Acad. Sci. U.S.A.*, 83:7023; Lasky et al., 1986, *Science*, 233:209) and a human (Zagury et al., 1986, *Nature* 326:249). Binding of the gp 120 molecule to the CD4 receptor also has been shown and monoclonal antibodies which recognize certain epitopes of the CD4 receptor have been shown to block HIV binding, syncytia formation, and infectivity. McDougal et al., (1986, *Science* 231:382) and Putney et al. (1986, *Science* 234:1392) elicited neutralizing serum antibodies in animals after immunizing with a recombinant fusion protein containing the carboxyl-terminal half of the gp 120 molecule and further demonstrated that glycosylation of the envelope protein is unnecessary for a neutralizing antibody response.

Shortly after HIV infection the immune system of man responds to the virus with both antibody production and cell mediated immune responses. A review of the immune responses to retroviruses has been published (Norley, S., and Kurth R., 1994: The Retroviridae, Vol E, J. A. Levy, ed., pp. 363–464, Plenum Press). Human antibodies specific for a number of HIV proteins including gp 160, gp 120, p66, p55, gp 41, p32, p24, and p17 have been reported (Carlson, 1988, J.Am. Med. Assoc. 206:674). The initial antibody response in man to HIV is directed to p17 and p24, followed by gp 120/160, then by gp 41, p66/55 and finally p32 (Lange, J. et al 1986, Br. Med. J. 292:228). As HIV infection progresses into AIDS antibody levels to p17 and p24 markedly fall to undetectable limits and are replaced by p17 and p24 antigenemia. Antibody titers to p32 and p55 also decline but to a lesser degree (McDougal et al 1987 J. Clin. Invest. 80:316). However, substantial amounts of antibodies to gp 160/120 persist throughout the entire course of HIV infection. During the early phases of HIV infection an elevation in total immunoglobulins is observed and this increased quantity of antibody is specific for HIV and predominantly directed to gp 120, (Amadori et al., 1988 Clin. Immunol.

Immunopathol. 46:342; Amadori et al, 1989, J. Immunol 143:2146). Possible mechanisms for this HIV specific hyper gamma globulinemia have been reviewed by Barker E. et al 1995: The Retroviridae Vol 4, J. A. Levy, ed. pp 1–96 Plenum Press. Functional properties and epitopes targeted by these antibodies produced during HIV infection have been described and include epitopes which are susceptible to antibody mediated neutralization. These primary target epitopes are primarily located on the envelope protein gp160 (gp120/gp41) and the gag protein p17; for review see Levy, 1994 Am.Soc. Micro; Nixon et al, 1992 Immunol 76:515. Neutralizing antibodies to HIV envelope protein have been identified and bind to conserved and divergent domains on gp 120. These include regions localized to the CD4 binding regions (Linsley et al 1988 and Thali et al, 1992); the second and third variable loop domains (Fung et al, 1992 and Haigwood et al 1990); and carbohydrate moieties (Benjouad et al, 1992 and Feizi and Larkin, 1990). Other neutralization sites have been identified on the external portion of gp 41 and a binding site on p17 (Changh et al, 1986). Early studies suggested that the presence of neutralizing antibodies lead to a more favorable clinical outcome, (Robert-Guroff et al, 1985). However, these studies employed selected sera with high neutralizing capacity against laboratory strains of HIV and not against autologous HIV isolates (Homsy et al, 1990; Tremblay and Wainberg, 1990). Subsequent investigation demonstrated that autologous antibody had little or no neutralizing activity against autologous HIV isolates (Homsy et al, 1990). The lack of susceptibility to antibody mediated neutralization in the presence of a neutralizing antibody is thought to result from the development of escape mutants that appear after seroconversion (Arendrup et al, 1992) and throughout the infection as new antibody specificities are produced. The clinical relevance of neutralizing antibodies produced as a consequence of HIV infection is unclear. However, it is clear that in spite of a vigorous immune response to HIV in individuals infected with HIV, progress to AIDS and, ultimately, death as a consequence of immune dysfunction predominates. Accordingly, new methods of treatment are sought.

OBJECTS OF THE INVENTION

It is an object of this invention to identify neutralizing regions of viral proteins which fail to elicit immune responses in man but do elicit immune responses in non-human mammals and to produce antibodies reactive with these regions. It is a further object of this invention to use these identified neutralizing regions of proteins and the antibodies reactive with them in the diagnosis, treatment and prevention of disease caused by the virus. Further objects of this invention will be apparent from the description of the invention detailed below.

SUMMARY OF THE INVENTION

In accordance with the present invention there are provided methods and compositions for the treatment, diagnosis and prevention of viral infection by the use of antibodies which react with regions of viral proteins to neutralize and inactivate functionally essential events in the life cycle of the virus. The antibodies recognize viral epitopes which fail to elicit an immune response in humans when encountered through infection or through environmental exposure but do elicit an immune response in non-human mammals.

Selected epitopes that react with nonhuman anti-viral antibodies but not with human anti-viral antibodies are identified. These epitopes escape surveillance by the human immune system through molecular mimicry to human proteins and in some instances are composed of amino acids susceptible to enzymatic cleavage in antigen processing cells. Desired epitopes are enzymatically cleaved by human enzymes and therefore are not processed for immune presentation.

Peptides representing these epitopes can be synthesized, optionally modified, and conjugated to a macrocarrier adjuvant to elicit antibody responses in non-humans. The preferred adjuvant is a microparticle comprising multiple repeats of muramyl dipeptide extracted from *Propionibacterium acini*.

Antibodies and peptides of this invention can be used in immunoassay configurations to identify species specific epitopes and to quantitate viral antigens in human tissues and fluids. In a preferred embodiment, the invention provides antibody and peptide compositions and methods useful in the treatment and diagnosis of individuals infected with the virus.

In a preferred embodiment, the virus of interest is HIV.

DETAILED DESCRIPTION OF THE INVENTION

The present invention provides novel compositions and methods for diagnosing and neutralizing viral infections. The invention will be described in detail with a focus on a preferred embodiment, in which the virus of interest is HIV. It is to be understood, however, that the principles of the invention can be used to identify neutralizing regions of proteins of other viruses and to produce antibodies reactive with those proteins that can be used to diagnose, treat and prevent infections caused by these other viruses as well.

Focusing now on HIV, this invention provides novel compositions and methods for neutralizing HIV infection and preventing or substantially inhibiting HIV infectivity, cell to cell transmission, and virus production in the infected host. More specifically, HIV protein sequences containing epitopes which fail to elicit an immune response in man when encountered through infection or naturally through the environment are utilized as described in detail below to produce antibodies in non-human mammals which can be administered to neutralize HIV infectivity, facilitate killing of infected CD4 lymphocytes, and inactivate essential steps in the life cycle of HIV. The term "neutralizing region" indicates those portions of HIV, particularly HIV proteins, containing amino acid segments defining one or more epitopes reactive with antibodies which, either individually or in combination with other antibodies of the present invention, are capable of neutralizing HIV infections. Suitable assays for evaluating neutralization are well known and can include assays which measure reduction of HIV infections in T-cell lines, reduction of plaque forming units of VSV (HIV) pseudo types bearing the envelope glycoproteins of HIV, syncytial inhibition tests, and virion-receptor binding tests. The term "inactivating region" indicates those segments of HIV proteins which contain one or more epitopes which when reacted with antibodies of this invention, either individually or in combination, inactivate functionally important events in the life cycle of HIV. Suitable assays to evaluate antibody-mediated destruction of HIV infected lymphocytes are well known and can include antibody dependent cell mediated cytotoxicity, complement mediated lysis, and natural killer (NK) assays. Suitable assays for measuring antibody-mediated inactivation of essential steps of the life cycle of HIV include assays which determine inactivation of reverse transcriptase, or measure polymerase and protease activity, or which evaluate antibody-mediated complement dependent changes in nuclear capsid permeability exposing viral RNA to ribonuclease degradation. As desired, the neutralizing activity can be compared to antibody reactivity in immunochemical assays, such as immunofluorescence, immunoblot, enzyme linked immunoassay, and radioimmunoassay.

The present invention is based on the discovery that epitopes which are functionally important in the life cycle of HIV, but not immunogenic in man, can be identified and characterized employing antibodies produced in selected mammalian species other than man. In addition, it has been discovered that the immunological non-responsiveness in man to these regions is a function of molecular mimicry and lack of MHC associated events, including antigen presentation through required MHC HLA class 1 and HLA class 2 associated events. With molecular mimicry the epitope is seen as self and is not responded to under normal circumstances. With lack of MHC associated events in antigen presentation several steps are involved and failure of any one step can result in the absence of an immunological response to the antigen.

Peptide regions containing multiple overlapping epitopes and antibodies to these epitopes have been produced and are shown to neutralize and inactivate essential steps in the life cycle of HIV in vitro. In addition, HIV-infected patients with AIDS have been treated with antibodies to these peptide regions, resulting in rapid reduction in blood born infectivity measured by total culturable infectious dose (TCID). Treatment of chronic AIDS patients with these antibodies has resulted in marked clinical improvement, including weight gain, resolution of opportunistic infections, decreased incidence and severity of infections and doctor visits and resolution of HIV-associated neuropathy. The patients further have shown immunological recovery, as defined by a reduction of HIV-RNA, increased CD4 number, increased CD8 number and restoration of the cytokine system associated with improved CD4 and CD8 numbers and function.

Identification of Epitopes and Production of Antibodies

The majority of immune reactions target immunodominant epitopes. HIV epitopes are most frequently identified and mapped by various immunological methods which employ antisera to HIV, cytotoxic T lymphocyte reactivity to HIV epitope targets and helper lymphocyte antigen presentation of HIV epitopes. Synthetic peptides of known sequence which mimic HIV sequence can be employed competitively or noncompetitively using well known assays to confirm these observations. It is to be understood that stimulation of the immune system can lead either to enhancement or suppression of the immune response. Factors which govern this include:

A. The sub population of lymphocytes stimulated by the immunogen (Suppressor versus Helper).
B. The micro-environment, including cell population residing therein, which contact the immunogen first.
C. The type of cytokines present in the micro-environment at the time of effector cell contact with the immunogen.
D. The type of cytokines elicited following effector cell contact with the immunogen.
E. Structural and biochemical composition of the immunogen.
F. The amino acid sequence of the immunogen and its susceptibility to protease degradation by proteases in the micro environment.

From preliminary experiments, the following properties were determined to be fundamentally important in determining the potential value of certain proteins and peptides for use in the production of antibodies which are intended for passive immunotherapy application in the treatment or palliation of disease processes in man and, in particular, infection with HIV at all stages including AIDS:

A. The immunogen must lack epitope determinants that are expressed on human cells and tissues when employed to produce antibody for use in passive immunotherapy with the following exceptions:
  1. Antigen distribution is restricted to sequestered and/or unavailable locations to the antibody.
  2. The antigen is expressed during developmental phases which permit the use of antibody at specific times during the developmental cycle, when antigen is not available.
  3. Epitope location within the host is not adjacent to a vital structure.
  4. Antigen distribution on host cell is at a density lower than required to produce injury but favorable on the desired target resulting in selective targeting.
  5. The target to normal ratio must be sufficiently different and favor antibody delivery to the desired target.
B. The number of peptide repeats delivered to an antigen-presenting cell directly influences the magnitude of the immunological response.
C. The epitope must not be present in body fluids at concentrations which would neutralize antibody and prevent targeting.

To date vaccine development has focused on designing better technology to amplify responses to targets to which the immune system of man responds, and passive immunotherapy has resulted in inconclusive results. Disclosed herein are alternate targets on HIV which do not elicit immune events in man as well as a new configuration to deliver antigen which results in immune reactions to HIV not previously attainable. The methods disclosed herein focus on the treatment of HIV and AIDS, but it is to be understood that the formulations of this invention have broad application. The antibody response in goats demonstrates utility of invention by way of antibody production to key targets on HIV, and by way of treatment which results in clinical improvement of AIDS. This technology has broad application in vaccine development.

Successful immune induction to antigen challenge requires the presentation of multiple epitope repeats by an antigen-presenting cell (APC) through MHC events. Epitopes which are most immunogenic are in an amphipathic configuration with a hydrophobic amino acid on one terminus, a hydrophilic amino acid on the other terminus, contain amino acids consistent with the formation of amphipathic helices; i.e., they lack helix breaking amino acids, such as proline, and lack carbohydrate. Sequences which lack amino acids that are susceptible to protease degradation by proteases in the micro-environment are especially desired.

To identify immunological targets on HIV with functional importance, immunogenic regions on HIV-related proteins in animal species other than man were determined. Goats were immunized with purified HIV lysate with and without carbohydrate groups removed. Removing carbohydrate residues from HIV proteins has little effect on the immunological response to the proteins yet can expose hidden epitopes. HIV lysates obtained commercially were further purified to remove proteins of tissue culture origins including human HLA class 1 antigens, HLA class 2 antigens, and beta-2-microglobulin. Following immunization, antisera from the goats were tested employing competitive immunoassay methodology to identify HIV peptides not recognized by antibodies pooled from HIV-infected patients. Pools of human HIV antisera were prepared from selected patient sera with high neutralizing and Western Blot activity and employed as competitive antibodies using standard competitive immunoassay methods. A broad spectrum of goat antibodies were identified which reacted with HIV determinants immunologically distinct from those recognized by the human anti-HIV antisera pools.

Those skilled in the art recognize that other animal species could be used to produce antibodies to these epitopes and that such antibodies could function in ADCC and complement mediated reactions. Other suitable animal species for the production of antibodies include, but are not limited to, sheep, rabbits, horses, cows and mice.

The epitope reactivity of the anti-HIV antibodies was characterized using twelve-mer peptides spanning the linear amino acid sequences of $HIV1_{SF2}$. Peptides of this size react well with antibodies, can be synthesized easily and can be prepared in highly purified form. Peptides were synthesized by and purchased from Purification Systems, Inc. The synthetic peptides were combined with peroxidase labeled goat anti-HIV antibodies and combined with each of two sets of microtiter wells coated with HIV. One set was blocked with human IgG anti-HIV; the other set was not. The percent of peptide inhibition of goat anti-HIV binding to HIV protein sites blocked with human anti-HIV was determined.

When inhibition of binding was observed with a specific synthetic peptide, additional peptides were synthesized with amino acid sequences overlapping that of the original inhibiting peptide to further define the epitope sequences.

The location of the epitopes on the HIV proteins recognized by goat anti-HIV IgG but not human anti-HIV IgG were further evaluated and confirmed using HIV peptide-HRP conjugates as the identification markers. In this assay, HIV proteins were absorbed to supports such as microtiter plate wells or precision polystyrene beads. Twelve-mer peptides spanning the linear amino acid sequence of $HIV1_{SF2}$ were covalently attached to horseradish peroxidase. Human and goat anti-HIV reactivity were measured independently with anti-HIV reactivity from human and goat bridging the native epitopes adsorbed to the support and to the peptide epitope covalently attached to peroxidase. With this procedure, detailed in Example 8, only exact epitopes contained within the synthetic peptide were recognized.

Once peptides having significant mimicry with human proteins have been identified, those sequences which have functional importance in the life cycle of HIV are determined. This is done, as described below and illustrated in Example 8, by generating antibodies to candidate peptides and then testing those antibodies for their effects on HIV infectivity and viral neutralization.

As noted above, a number of specific epitope regions have been identified and nine are described in detail below with reference to the $HIV1_{SF2}$ sequence unless otherwise indicated. Amino acid residue designations set forth below and throughout this application for $HIV1_{SF2}$ are from the Los Alamos Data Bank (AIDS Virus Sequence Data Base, Los Alamos National Laboratories, Theoretical Division, Los Alamos, N. Mex. 87545). Amino acid residue designations set forth below and throughout this application for $HIV2_{NZ}$ are from the Ex Pasy World Wide Web Molecular Biology Server of the Geneva University Hospital and the University of Geneva, and the BioAccelerator available through Compugen Ltd. at the Weizman Institute, Israel, and Akira Ohyama, BioScience Systems Department, Mitsuey Knowledge Industry Co., Ltd., Tokyo, Japan. Those skilled in the art will appreciate that additional analogous regions ("homologs") from other HIV isolates can be identified based upon their location within related proteins from various isolates. In practice, such homologs can be identified by reference to $HIV1_{SF2}$ sequence data as follows:

(a) the amino acid sequences of HIV isolates and $HIV1_{SF2}$ can be aligned to obtain maximum homology between the two sequences, generally at least about 75% identify between the sequences;

(b) once an amino acid sequence is aligned to the corresponding location within $HIV1_{SF2}$ proteins will demonstrate immunological mimicry, similarity, or identity with $HIV1_{SF2}$ as defined by retention of antibody reactivity to the mimicked or homologous sequence. Peptides from other HIV isolates and their amino acid sequences so identified typically will immunologically mimic corresponding regions on $HIV1_{SF2}$.

This method of identifying key epitopes can be applied to HIV strains that are yet to be discovered. For example, as new strains of HIV are identified, their envelope and core amino acid sequences can be aligned with that of $HIV1_{SF2}$ to obtain maximum sequence homology with that strain. The methods by which the sequences are aligned are known to those skilled in the art. In aligning the sequences it is desired to maintain as much homology between cysteine residues as possible. The amino acid sequence(s) of the new HIV strain or species which corresponds to the location of the peptides specifically disclosed herein can be synthesized and used in accordance with the invention.

It is not necessary to the present invention that the epitopes contained within such sequences be cross-reactive with antibodies to all strains or species of HIV. Peptides encompassing immunological epitopes which distinguish one species or serogroup over another will find utility in identifying particular species or serogroups and may assist in identifying individuals infected with one or more species or serogroups of HIV. They also can be useful in combination with other peptides, from either a homologous region or another neutralizing region, in therapeutic regimens.

The amino acid sequences of this invention typically comprise from about 5 to about 50 amino acids and comprise an epitope region or multiple epitope regions located on HIV proteins that fail to elicit a protective immune response in man when encountered through infection or environmental contact but do elicit a response in a non-human mammal. Preferably, the sequences comprise between about 5 and 35 amino acids. Synthetic peptides or treated lysates of natural HIV proteins containing the desired amino acid sequences are used to immunize animals which respond immunologically to them and produce antibodies which have therapeutic value in treating HIV infections.

The amino acid sequences or peptides of interest fail to elicit an immune response in man through mimicry of epitopes on human and other proteins. Of particular interest are peptide epitopes shared between HIV proteins and human alpha fetoprotein, aspartyl protease, deoxyuridine 5'-triphosphate nucleotidohydrolase, eosinophil cationic protein, eosinophil-derived neurotoxin and ribonuclease 4 precursor and peptide epitope regions mimicked by neurotoxins from Bungaris Naja, Dendoaspis, Psudechis, or Androctonus Centruroides.

In the discussion which follows, reference is made to a number of human proteins and neurotoxins using standard identifying abbreviations for the proteins. Set forth below is a table which sets forth these abbreviations and the full names of the proteins to which they correspond:

Human Proteins With Sequence Similarity to HIV Proteins

Swiss Prot ID
XXXX-Human    Protein

| | |
|---|---|
| ACE | angiotensin-converting enzyme precursor |
| ACHE | acetyl choline receptor protein |
| 3BH1 | 3-beta hydroxy-5-ene steroid dehydrogenase type I |
| 3BH2 | 3-beta hydroxy-5-ene steroid dehydrogenase type II |
| 41BL | 4-1BB ligand |
| BLSA | beta-lymphocyte antigen precursor |
| CATD | cathepsin D precursor |
| CD69 | early activation antigen CD69 |
| CD81 | CD81 antigen |
| CO02 | tumor-associated antigen CO-029 |
| CP11 | cytochrome P450 IA1 |
| CYRP | cytokine receptor common beta-chain precursor |
| CYPC | peptidyl-prolyl cis-trans isomerase C |
| DIAC | di-N-acetylchitobiase precursor |
| DUT | deoxyuridine 5'-triphosphate nucleotidohydrolase |
| ECP | eosinophil cationic protein precursor |
| EV2B | ectotropic viral integration site 2B protein |
| FETA | alpha fetoprotein |
| FOL1 | folate receptor alpha precursor |
| GSHR | glutathione reductase |
| IL9 | interleukin 9 precursor |
| IN19 | interferon-inducible protein 9-27 |
| INIU | interferon-inducible protein I-8U |
| INR2 | interferon alpha/beta receptor beta-chain precursor |
| KLTK | leukocyte tyrosine kinase receptor precursor |
| KPCL | eta type protein kinase C |
| LBP | lipopolysaccharide binding protein precursor |
| LCAT | lecitnin-cholesterol acyltransferase |
| LECH | asialoglycoprotein receptor 1 |
| LFA3 | lymphocyte function-associated antigen-3 precursor |
| LMA1 | lamanin alpha-1 chain precursor |
| LONN | mitochondrial LON protease homolog precursor |
| LONM | mitochondrial LON protease homolog precursor |
| LYOX | protein-lysine 6-oxidase precursor |
| MAG1 | melanoma associated antigen 1 |
| MAG2 | melanoma associated antigen 2 |
| MAG3 | melanoma associated antigen 3 |
| MC5R | melanocortin-5 receptor |
| MYSE | embryonic myosin heavy chain |
| NOL1 | proliferating-cell nucleolar antigen P120 |
| NRM1 | natural resistance-associated macrophage protein 1 |
| NT3 | neurotrophin-3 precursor |
| NTCR | sodium and chloride-dependent creatin transporter 1 |
| NXS1-NAJAT | cobrotoxin |
| PA2M | membrane associted phospholipase A2 precursor |
| PIP5 | phospholipase C-gamma-2 |
| PGDS | alpha-platelet derived growth factor precursor |
| PLK | proteoglycan link protein precursor |
| POL1 | retrovirus-related pol polyprotein |
| PSS1 | phosphatidylserine synthease I |
| RENI | renin precursor |
| RNKD | nonsecretory ribonuclease precursor |
| S5A2 | 3-oxo-5-alpha-steroid-4-dehydrogenase 2 |
| SDC1 | syndecan-1 precursor |
| SDC4 | syndecan-4 precursor |
| SEMI1 | semenogelin 1 protein precursor |
| SON | SON protein |
| SPCB | erthrocyte spectrin beta-chain |
| SRE1 | sterol regulatory element binding protein 1 |
| SYV | valyl-tRNA synthetase |
| TCO2 | transcobalin II precursor |
| TGL3 | protein-glutamine glutamyltransferase E3 precursor |
| TFPI | tissue factor pathway inhibitor precursor |
| TRFL | lactotransferrin precursor |
| TYK2 | non-receptor tyrosine-protein kinase |
| VPRT | retrovirus related protease |
| WNT2 | WNT-2 protein precusor |
| ZN45 | zinc finger protein 45 |

The amino acid sequences of nine of the highly conserved epitope regions discussed above are provided below. Three of these regions are on the envelope glycoproteins gp120 (two targets) and gp41 (one target), one is on the reverse transcriptase heterodimer p66/55, and one is on protease p10. Additional targets are on the Gag precursor (p55/Gag) with sites on p17 (two targets), p24 and p7.

One epitope region on $HIV1_{SF2}$ gp120 extends from amino acid residue 4 through 27 and a second extends from amino acid residue 54 through 76 of HIV1. Antibodies to epitope regions located on gp120 function synergistically to effect the release of gp120 from gp41. The release of gp120 from gp41 is antibody dose dependent and can be demonstrated by neutralization assays, such as TCID, which measure HIV infectivity.

An epitope region of a neutralizing or inactivating region of gp120 of $HIV2_{NZ}$ also has been determined. The sequence of $HIV2_{NZ}$ envelope glycoprotein gp120 has been mapped, and from about amino acid residue 7 through 43 is a region mimicking a sequence of $HIV1_{SF2}$ gp120 and certain human proteins. Antibody targeting the region results in dissociation of HIV2 gp120 from gp41, which correlates with a reduction in infectivity.

A third HIV envelope glycoprotein target for $HIV1_{SF2}$ was located at amino acid residues 502–541 of gp41 transmembrane glycoprotein. Antibody targeting of this region in the presence of complement results in an antibody dependent complement mediated lysis of the HIV envelope glycoprotein and marked reduction in HIV infectivity.

In addition to the envelope glycoprotein epitope regions, another HIV1 epitope region of interest includes amino acid residues 254 through 295 of the reverse transcriptase heterodimer p66/55. Antibody targeting of this region results in an antibody dose dependent reduction in reverse transcriptase activity. Also of interest is the epitope region encompassing amino acid residues 69–94 of protease p10. Antibody targeting of this region results in an antibody dose dependent reduction in protease activity.

The targets on reverse transcriptase and protease are in conserved regions adjacent to the enzyme active site, which is well-known for its mutation and subsequent resistance to competitive inhibitors. The antibody-mediated inactivation results from a steric or conformational change in the enzyme with secondary loss of activity. This method of inactivation functions independently and is not influenced by mutation in the enzyme active site and is irreversible.

Also of interest are three epitope regions within the Gag gene. Specifically, amino acid residues 166 through 181 of Gag gene protein p24, one target at amino acid residues 2 through 23 and a second target at amino acid residues 89 through 122 of Gag gene protein p17 and amino acid residues 390 through 410 and 438 through 443 of Gag gene protein p7 are useful in this invention. Antibodies targeting these regions result in disruption of the nuclear capsid following lysis of the HIV envelope by the antibodies described above. This targeting culminates with exposure of HIV RNA to plasma RNAse degradation. Additionally, the targets on p17 is exposed on the surface of infected lymphocytes following budding. This provides an additional target for ADCC lysis of infected lymphocytes.

One of the specific peptides set forth above, comprising at least one epitope not recognized by antibodies from HIV-infected patients but recognized by goat anti-HIV antibodies, is the peptide comprising amino acid residues 4 through 27 of $HIV1_{SF2}$ envelope gp120 protein and linear epitope-containing subsequences thereof, which has the following sequence:

K G T R R N Y Q H L W R W G T L L L G M L M I C
This peptide mimics human proteins FOL1, NTCR, PIP5, PSS1, KLTK, MC5R, ECP, INIU, INI9, VPRT, CD69, MYSE, RNKD, ACHE, TCO2, LCAT, MAG1, MAG2, MAG3 and LYOX.

A second epitope region from the HIV1$_{SF2}$ gp120 envelope glycoprotein extends from amino acid residue 54 through 76, which has the sequence:

A S D A R A Y D T E V H N V W A T H A C V P T

This peptide mimics proteins CYRB and SYV.

A third epitope region of interest in the envelope of HIV1$_{SF2}$ extends from amino acid residue numbers 502 through 541 of glycoprotein gp41. This peptide has the following amino acid sequence:

| HIV1_Env502 | | | | | | | | | | | | |
|---|---|---|---|---|---|---|---|---|---|---|---|---|
| R | V | V | Q | R | E | K | R | A | V | G | I | V | G | A | M |
| F | L | G | F | L | G | A | A | G | S | T | M | G | A | V | S |
| L | T | L | T | V | Q | A | R | | | | | 502-541 | | | |

This peptide mimics human proteins CYPC, TYK2, ACHE, NTCF, NTCR, CD81, 41BL, NIDO, GSHR, CO02 and TCO2.

In another specific embodiment, an epitope region of interest is that of amino acid residues 2 through 23 of the HIV1$_{SF2}$ Gag protein p17. This peptide has the sequence:

G A R A S V L S G G E L D R W E K I R L R P

This peptide mimics human proteins TFPI, PA2M, BLSA, ECP, and FETA and certain neurotoxins, such as NXS1 and NAJAT. The peptide has a hydrophobic sequence which binds to and targets host cell membrane and function mimics cellular translation protein Src.

A second target on HIV1$_{SF2}$ p17 extends from amino acid residue 89 through 122. This peptide has the sequence:

L Y C V H Q R I D V K D T K E A L E K I E E E Q N K S K.

This peptide mimics FETA and TRIC.

Another peptide of interest is that of amino acid residues 166 through 181 of the Gag gene protein p24 and epitope containing subsequences therein. This peptide has the sequence:

P E V I P M F S A L S E G A T P

This peptide mimics human proteins FETA and TRFL.

A third Gag gene protein epitope region of interest is the peptide having amino acid residues 390 through 410 and 438–443 of Gag gene protein p7 and epitope containing subsequences thereof. This peptide has the sequence:

K T V K C F N C G K E G H I A K N C R A P+K I W S S Q

This peptide mimics human FETA and RNA binding proteins. This peptide contains a zinc binding domain which interacts with, and binds to, viral RNA. Antibodies to this region enhance the removal of premature HIV devoid of envelope following the lysis of infected CD4+ lymphocytes.

Also of interest as an epitope region is the peptide of amino acid residues 69 through 94 of the protease p10 and epitope-containing subsequences thereof. This peptide has the sequence:

R I G G Q L K E A L L D T G A D D T V L E E M N L P

This peptide sequence mimics human proteins RENI, BLSA, VPRT and CATD. Antibodies to this sequence inhibit the protease activity of HIV.

A further specific sequence useful in this invention is a sequence encompassing amino acid residues 254 through 295 of HIV1 reverse transcriptase heterodimer p66/55. This peptide has the sequence:

G L K K K K S V T V L D V G D A Y F S V P L D K D

F R K Y T A F T I P S I N N E T P

This peptide sequence mimics human proteins POL1 and ECP.

As noted above, other strains of HIV also can be used to obtain peptides and antibodies in accordance with the present invention. Useful peptides from other strains can be determined by comparing and aligning the sequence of another strain to the sequence of HIV1$_{SF2}$ or HIV2$_{NZ}$ and finding that part of the sequence homologous to the epitopes of interest identified for HIV1$_{SF2}$ or HIV2$_{NZ}$.

A sequence of interest in HIV2$_{NZ}$ identified by the method of this invention is in the env gp120 open reading frame and extends from amino acid residue numbers 7 through 43. This peptide has the following sequence:

Q L L I A I V L A S A Y L I H C K Q F

V T V E Y G I P A W R N A S I P L F

This peptide mimics human proteins IL9, SRE1, NRM1, LBP, NOL1, S5A2, LMA1, LECH, LFA3, KPLC, FETA, 3BH2, 3BH1, INR2 and EV2B.

For example, once the desired amino acid sequences have been identified, antibodies which recognize these sequences are obtained. Such antibodies can be obtained using proteins containing the peptides isolated from HIV lysates, synthetic peptides, bacterial fusion proteins and proteins/peptides from phylogenetically unrelated sources which contain the desired epitopes.

If viral lysates are to be used, a protein lysate of a single HIV strain can be used, or a mixture of lysates of two or more different strains can be used. If a mixture of lysates is used, the mixture can comprise lysates of different HIV1 strains or a combination of at least one HIV1 strain and at least one HIV2 strain. A preferred mixture is a combination of lysates from HIV1$_{BAL}$, HIV1$_{MN}$ and HIV2$_{NZ}$.

Viral lysates initially are treated to remove lipids and other impurities from the HIV proteins. The HIV protein mixture then is treated to remove contaminants of cell culture origin, including human leukocyte antigen (HLA), class I and class II antigens. Methods for removing these antigens are known in the art and include employing monoclonal anti-HLA class I and anti-HLA class II antibodies and immunoaffinity procedures; one method is set forth in detail in Example 3 below.

In addition, it has been found that carbohydates of the HIV proteins must be removed; phylogenically preserved carbohydrates determinants otherwise would stimulate immune responses when the HIV proteins are administered to an animal, resulting in the production of antibodies which would be cytotoxic against human tissues. The proteins are treated with enzymes known to those skilled in the art to remove carbohydrates, including PGNase, neuraminidase and glycosidase. One such method is described in detail in Example 3.

The mixture of treated HIV proteins then can be used to immunize an animal to produce antibodies to the peptides of interest. Desirably, the mixture contains approximately equal amounts of the proteins comprising the peptides or epitope regions of interest. That is, desirably they are provided in proportions of approximately 1:1 and the difference in molar ratios between any two peptides is no greater than about 10:1, preferably 3:1.

Alternatively, synthetic peptides can be used as the immunogen. If synthetic peptides are used the amino acid sequence of any desired peptide can be modified by, for example, using a substituted or truncated form of the amino acid sequence.

Amino acid substitutions can be made to avoid predicted enzymatic cleavage that can occur during antigen processing at a particular amino acid moiety, to force amphipathic conformation to meet required MHC-associated antigen presentation and to provide sufficient length for HLA presentation should cleavage occur at or near the epitope boundary. Truncated sequences are selected such that the peptide will retain conformity to epitope length requirements as predicted by MHC class 1 and class 2 antigen presentation motifs. More extensive guidelines on desirable amino acid substitutions are given below as part of the section on synthetic peptides. In addition to substituted and truncated sequences, extended sequences can be prepared in which additional amino acids are added at either end of a selected epitope region for the purpose of facilitating attachment to solid phase supports and macromolecular carriers.

As an example, useful truncated sequences of the peptide extending from amino acid residue 502 through 541 of $HIV1_{SF2}$ gp41 discussed above include a peptide with the sequence of amino acid residues 512–531:

G I V G A M F L G F L

G A A G S T M G A and also a sequence extending from amino acid residue 518 through amino acid residue 527:

F L G F L G A A G S

Another particularly useful truncated peptide is a truncated sequence of the peptide extending from amino acid 7 through 43 of gp120 of $HIV2_{NZ}$ has the following sequence

L L I A I V L A S A Y L I H C K Q

The peptide can be prepared in a wide variety of ways. The peptide, because of its relatively small size, can be synthesized in solution or on a solid support in accordance with conventional techniques. Various automatic synthesizers are commercially available today and can be used in accordance with known protocols. See, for example, Stewart and Young, *Solid Phase Peptide Synthesis*, 2nd ed., Pierce Chemical Co., 1984; and Tam et al., *J. Am Chem. Soc.* (1983) 105:6442.

Alternatively, hybrid DNA technology can be employed where a synthetic gene is prepared by employing single strands which code for the polypeptide or substantially complementary strands thereof, where the single strands overlap and can be brought together in an annealing medium so as to hybridize. The hybridized strands then can be ligated to form the complete gene, and, by choice of appropriate termini, the gene can be inserted into an expression vector, many of which are readily available today. See, for example, Maniatis et al., *Molecular Cloning, A Laboratory Manual*, CSH, Cold Spring Harbor Laboratory, 1982. Or, the region of the viral genome coding for the peptide can be cloned by conventional recombinant DNA techniques and expressed in procaryotic or eukaryotic expression systems to produce the desired peptides.

Preferably, the immunogen will be enriched for the desired epitopes to which antibody-producing B lymphocytes will respond by producing antibodies that will neutralize and inactivate essential steps in the life cycle of HIV infection. As used herein, "enriched" means that a desired epitope constitutes at least 25% of the HIV protein, preferably at least 50%, and most preferably about 95%. More particularly, solutions containing disrupted virus lysate or extracts, or supernatant of biologically-expressed recombinant proteins or disrupted expression vectors or proteins containing mimicked epitopes can be enriched for such proteins, as desired, using purification methods, such as, for example, polyacrylamide gel electrophoresis. Immunoaffinity purification is a preferred and convenient method for purification of proteins and peptides containing the desired HIV epitopes, e.g., affinity purification using mono specific affinity purified polyclonal or monoclonal antibodies. The extent to which the peptides are purified from the solutions for use as an immunogen can vary widely, i.e., from about 50%, typically at least 75% to 95%, desirably 95% to 99% and, most desirably, to absolute homogeneity.

To obtain antibodies to the desired epitopes, animals are immunized with either the peptides of interest or HIV proteins containing them which have been treated to remove carbohydrates and HLA antigens as disclosed above. Immunization protocols are well known and can vary considerably yet remain effective. See Colco, *Current Protocols in Immunology*, John Wiley and Sons, Inc. 1995. The proteins and/or peptides can be suspended or diluted in an appropriate physiological carrier for immunization. Suitable carriers are any biologically compatible, non-toxic substance to deliver and/or enhance the immunogenicity of the peptides, including sterile water and 0.9% saline.

Alternatively, the peptides can be coupled to a carrier molecule before being used as an immunogen. One preferred technique, for example, discussed in more detail below, involves the attachment of the proteins and fragments thereof to multiple repeats of a glycopeptide, such as muramyl dipeptide (MDP), to form a microparticle, typically less than 1 micron, and preferably less than 0.2 microns, in diameter. The microparticle then can be dispersed in a pharmaceutical carrier for injection. This procedure achieves a high density of the peptide which can be used to elicit the desired immune response. The selection of carrier will vary depending upon the route of administration and response. The compositions can be sterilized by conventional, well-known sterilization techniques. The peptides can be administered by oral or parenteral routes, preferably the latter.

Immunogenic amounts of antigenic preparations enriched for the desired epitopes are injected, generally at concentrations in the range of 1 µg to 20 mg/kg body weight of host. Administration can be by injection, e.g., intramuscularly, peritoneally, subcutaneously, intravenously, etc. Administration can be one time or a plurality of times, usually at one to four week intervals.

Immunized animals are monitored for production of antibody to the desired epitope. High affinity complement fixing IgG antibody is preferred for passive immunotherapy and can be used intact or as fragments such as Fv, Fab, F(ab')$_2$. Antibody fragments may be preferable when greater tissue penetration is desirable. Antibodies and fragments can be given alone or as conjugates with toxic substances or isotopes. Once the desired antibody response is attained, blood is collected by, for example, venipuncture, cardiac puncture, or plasmapheresis. Antibodies are purified from the complex serum or plasma mixture in accordance with conventional procedures, including, for example, salt precipitation, ion exchange chromatography, size chromatography, affinity chromatography. Oftentimes, a combination of methods is used. Immunoaffinity chromatography is a preferred method.

To circumvent possible antigenicity in a human receiving antibody derived from a non-human animal, recombinant antibodies can be constructed. One type of recombinant antibody is a chimeric antibody, wherein the antigen binding fragment of an immunoglobulin molecule (variable region) is connected by a peptide linkage to at least part of another protein not recognized as foreign by humans, such as the constant portion of a human immunoglobulin molecule. This can be accomplished by fusing the animal variable region exons with human kappa or gamma constant region exons. Various techniques are known to the skilled artisan, such as those described in PCT 86/01533, EP171496, and EP173494, the disclosures of which are incorporated herein by reference. A preferred type of recombinant antibodies is CDR-grafted antibodies.

PHARMACEUTICAL FORMULATIONS AND THEIR USE

The antibodies of this invention that neutralize infectivity, kill infected CD4 lymphocytes and inactivate functionally important events in the life cycle of HIV are incorporated as components of pharmaceutical compositions. The compositions comprise a therapeutic or prophylactic amount of at least one of the antibodies of this invention, and desirably an antibody cocktail, with a pharmaceutically acceptable carrier. A pharmaceutically acceptable carrier is any compatible, non-toxic substance suitable for the delivery of the antibodies to the patient. Thus, this invention provides compositions for parenteral administration which comprise a solution of antibody dissolved in an acceptable carrier, preferably an aqueous carrier. A variety of aqueous carriers can be used, e.g., water, buffered water, 0.4% saline, 0.9% saline, 0.3% glycine and the like. These solutions are sterile and generally free of particulate matter. The compositions further can comprise pharmaceutically acceptable auxiliary substances as required to approximate physiological conditions, such as pH adjusting and buffering agents, toxicity adjusting agents and the like. For example, sodium acetate, sodium chloride, potassium chloride, calcium chloride, sodium lactate, etc., can be used. The concentration of antibody in these formulations can vary, typically from less than about 0.1 mg/ml to as much as 150 or 200 mg/ml, preferably between about 1 mg/ml and about 20 mg/ml, and will be selected primarily based on fluid volumes, viscosities, etc., preferably for the particular mode of administration selected. Determining the concentration of a particular antibody or antibody cocktail is within the abilities of one of ordinary skill in the art. Thus, a typical pharmaceutical composition for intravenous infusion can be made up to contain 250 ml of sterile Ringer's solution and 100–200 mg of antibody. Compositions for intramuscular injection can be made up to contain 1 ml sterile buffered water and about 20 to about 50 mg of antibody. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference. Such compositions can contain a single antibody which is, for example, specific for certain strains of HIV or for a single protein or glycoprotein expressed by most and, more preferably, all strains of HIV. Alternatively, a pharmaceutical composition can contain more than one antibody to form a "cocktail." For example, a cocktail containing antibodies against various proteins and strains of HIV would be a universal product with therapeutic or prophylactic activity against the great majority of the clinical isolates of HIV. The cocktail can contain antibodies which bind to epitopes on proteins or glycoproteins of the HIV envelope, for example, or can contain a combination of antibodies to epitope sites identified above on HIV1$_{SF2}$ Env proteins gp160, gp120, and gp41; Gag protein p7, p17 and p24; reverse transcriptase heterodimer p66/55 and protease p10, or a subgroup thereof, thus neutralizing a series of epitopes crucial in the life cycle of HIV. Antibodies to epitope sites on other neutralizing or inactivating regions of HIV proteins also, of course, can be employed.

For example, antibodies which modify attachment, cell entry, transcription, translation, assembly, targeting of the mature virion to the plasma membrane and extrusion of the virion will interfere with HIV life cycle events. Antibody cocktails will more frequently be employed to obtain inactivation of multiple essential HIV proteins. This will be of therapeutic benefit in particular within virions lacking the outer envelope but possibly are infectious should they gain cell entry by other mechanisms such as micro-pinocytosis or transfection or the like. The molar ratio of the various antibody components usually will not differ by more than a factor of 10, more usually by not more than a factor of 5, and will usually be in a molar ratio of about 1:1–3 to each of the other antibody components.

With respect to antibodies to the nine specific peptides set forth above, a desirable antibody cocktail comprises antibodies to the two envelope gp120 peptides and gp41 peptide. More desirably, the cocktail comprises antibodies to those three epitope regions plus an antibody to the protease p10 epitope region. Even more desirably, the cocktail comprises antibodies to those four epitope regions plus antibodies to at least one of the other five enumerated epitope regions. In a most preferred embodiment, the cocktail comprises antibodies to all nine of the epitope regions.

The antibodies and antibody cocktails of the present invention can be administered independently or given in conjunction with other anti-retroviral agents. The current status of the development of other anti-retroviral agents, and of anti-HIV agents in particular, is reviewed in Mitsuya et al., *Nature* 325:773–778, 1987.

The antibodies and peptides of this invention can be stored in liquid format at various temperatures known to preserve antibody activity, e.g. −70° C., −40° C., −20° C., and 0–4° C. or lyophilized for storage and reconstituted in a suitable carrier prior to use. This technique has been shown to be effective with conventional immune globulins, purified antibodies, and immunogens composed of proteins, glycoproteins, and peptides. Art-known lyophilization and reconstitution techniques can be employed and it will be appreciated by those skilled in the art that lyophilization and reconstitution can lead to varying degrees of antibody activity loss (e.g., with conventional immune globulins, IgM antibodies tend to have greater activity loss than IgG antibodies) and that doses may have to be adjusted to compensate for any loss.

The compositions containing the present antibodies or cocktails thereof can be administered for the therapeutic and/or prophylactic treatment of HIV infections. In therapeutic application, compositions are administered to a patient already infected with HIV, in an amount sufficient to treat or at least partially arrest the infection and its complications. An amount adequate to accomplish this is defined as a "therapeutically effective dose." Amounts effective for this use will depend upon the severity of the infection and the general state of the patient's own immune system, but generally range from about 0.1 to about 200 mg of antibody per kilogram of body weight with dosages of from 0.5 to 25 mg per kilogram being preferred. The compositions of this invention can be employed in serious disease states that are life-threatening or potentially life-threatening situations. In such cases, it is possible and may be felt desirable by the treating physician to administer substantial excesses of these antibodies.

In prophylactic applications, compositions containing the present antibodies or a cocktail thereof are administered to a patient not already infected by HIV, but perhaps recently exposed to or thought to have been exposed to, or at risk of being exposed to the virus (such as, for example, the newborn of an HIV infected individual), or immediately following an exposure or suspected exposure to HIV. If the composition is to be administered to an HIV-infected pregnant female, it can be given once or multiple times prior to delivery to reduce HIV infectivity in maternal blood and thereby reduce the risk of HIV transmission to the newborn. The newborn at risk also can be treated to further reduce the risk of contracting HIV. An amount defined to be a "prophylactically effective dose" generally ranges from 0.1 mg to 25 mg per kilogram of body weight, depending upon the patient's state of health and general level of immunity.

In addition, the antibodies of the present invention can find use as a target-specific carrier molecule. An antibody can be bound to a toxin to form an immunotoxin or a radioactive material or drug to form a radiopharmaceutical or pharmaceutical. Methods for producing immunotoxins and radiopharmaceuticals are well known (see, for example, Cancer Treatment Reports 68:317 (1984)). Heteroaggregates of antibodies of the present invention and human T-cell activators, such as monoclonal antibodies to the CD3 antigen or to the Fc gamma receptor on T-cells, can enable human T-cells or Fc-gamma bearing cells (such as K cells or neutrophils) to kill HIV infected cells via antibody dependent cell-mediated cytolysis (ADCC). Such heteroaggregates can be assembled, for example, by covalently cross-linking the anti-HIV antibodies to the anti-CD3 antibodies using the heterobifunctional reagent N-succinimidyl-3-(2-pyridyl dithiol)propionate, as described in Karpowsky et al., *J. Exp. Med.* 160:1686 (1984), which is incorporated by reference herein.

Other anti-HIV agents also can be included in the formulations, such as 3'-azido-3'-deoxythymidine, 2',3'-dideoxycytidine, 2',3'-dideoxy-2',3'-didehydrocytidine, etc.

In addition to antibody compositions, compositions comprising the peptides of this invention can be administered for therapeutic and prophylactic vaccination of HIV-infected individuals. For therapeutic application, compositions comprising peptides, either as isolated peptides optionally modified as discussed above or contained within HIV proteins treated as described above and desirably coupled to an MDP microparticle to further stimulate immunogenicity, are administered to a patient infected with HIV. The amount of peptide administered is chosen so as to stimulate antibody production to functional HIV epitopes not previously recognized by the patient's immune system so that the stimulated antibodies can arrest the infection. In prophylactic applications, compositions of the peptides coupled to the microparticle MDP are administered to persons not infected with HIV to stimulate the production of antibodies against otherwise unrecognized epitopes to provide a protective function against future infection.

DIAGNOSTIC AND PROGNOSTIC USES OF ANTIBODIES AND ANTIGEN

The antibodies and epitopes recognized by them and disclosed in the present invention also are useful for the diagnosis and management of HIV infection. Typically, diagnostic assays employing antibodies and/or their respective antigens entail the detection of the antigen-antibody complex. Numerous immunoassay configurations have been described and employ either labeled or unlabeled immunochemicals for this purpose. When unlabeled, the antibodies find use, for example, in agglutination assays, antibody dependent complement mediated cytolysis assays, and neutralization assays. Unlabeled antibodies can be used in combination with other, labeled, antibodies (second antibodies) that are reactive with the primary antibody, such as antibodies specific for immunoglobulin. Unlabeled antibodies can be used in combination with a labeled antibody which is reactive with a non-competitive epitope on the same antigen, such as in sandwich type immunoassays, or in combination with a labeled antigen. Alternatively, the antibodies can be directly labeled and used in both competitive and non-competitive immunoassays. These assay types and configurations are well known in the art. A wide variety of labels can be employed, such as radioisotopes, fluorescent tags, enzymes, enzyme substrates, enzyme cofactors, enzyme inhibitors, ligands (particularly haptens), etc. Numerous types of immunoassays are available and, by way of example, include those described in U.S. Pat. Nos. 3,817,827; 3,850,752; 3,901,654; 3,935,074; 3,984,533; 3,996,345; 4,034,074; and 4,098,876.

Commonly, the antibodies and peptides of the present invention are utilized in enzyme immunoassays, where, for example, the subject antibodies, or their respective antigens are conjugated to an enzyme and the immunoassay is configured to provide maximal sensitivity and specificity in detecting HIV antigens in biological samples such as human blood serum, saliva, semen, vaginal secretions or viral infected cell culture suspension.

Kits also can be designed for use with the subject antibodies for use in the detection of HIV infection or the presence of HIV antigen. The kits comprise antibodies of the present invention optionally in conjunction with additional antibodies specific for other epitopes of HIV. The antibodies, which can be conjugated to a label, unconjugated or bound to a solid support such as the surface of a microtiter plate well or a polystyrene bead, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient can be present in from about 1% to 99% wt. of the total composition. Where a second antibody capable of binding to the antibody is employed, the second antibody usually will be present in a separate vial. The second antibody typically is conjugated to a label and formulated in an analogous manner with the antibody formulations described above. The subject epitope recognized by the antibody can be provided labeled or non-labeled and can be provided as part of a larger protein (synthetic, recombinant, or native), with or without modification such as the addition of spacer arms, amino groups, or cysteine residues, which can be used to attach the peptide to a support and extend it from the surface of the support. Such modifications are employed to provide the epitope in an arrangement to optimize immunoreactivity with the antibody. Such peptides are formulated in a manner analogous to that of the epitope-containing proteins as described above.

The detection of HIV antigens, or the whole virus, in various biological samples is useful in diagnosing a current infection by HIV, evaluating response to therapy, enumerating infected cells, serotyping HIV strains (clades), identifying and quantitating virulence factors associated with primary infection, progression and complications such as peripheral neuropathy, multi focal leukoencephalopathy, and Kaposi's sarcoma. Biological samples can include, but are not limited to, blood, serum, saliva, semen, tissue biopsy samples (brain, skin, lymph nodes, spleen, etc.), cell culture supernatants, disrupted eukaryotic and bacterial expression systems, and the like. Presence of virus, viral antigens, virulence factors, and serotyping determinants are tested for by incubating the antibody with the biological sample under conditions conducive to immune complex formation, followed by the detection of complex formation. In one embodiment, complex formation is detected through use of a second antibody capable of binding to the primary antibody and typically conjugated to a label. The second antibody is formulated in a manner analogous to that described for the primary antibody formulations described above. In another embodiment, the antibody is attached to a solid phase support which then is contacted with a biological sample. Following an incubation step, labeled antibody is added to detect the bound antigen. In another embodiment, the antibody is conjugated to a detection label and following an incubation step with a biological sample, such as cells or tissue sections, the sample is evaluated by flow cytometry or microscopy for the antigen.

PREPARATION AND USE OF SYNTHETIC PEPTIDES

Peptides of this invention can be modified by introducing amino acid substitutions into the peptide. Substitutions may be desirable to vary one or more particular amino acids to more effectively mimic the epitopes of the different retroviral strains or to enhance immunological responses or MHC interactions with the epitope resulting in greater immunogenicity of the mimicked epitope when used for immunization or vaccination. In addition, it can be desirable to make certain amino acid substitutions to enhance the chemical stability of the peptide.

More specifically, a polypeptide employed in the subject invention need not be identical to any particular HIV polypeptide sequence, so long as it is able to provide immunological competition with proteins of at least one of the strains of HIV. Therefore, the subject polypeptides can be subject to various changes, such as insertions, deletions, and substitutions, either conservative or non-conservative, where such changes will enhance the desired activity of the peptide. Conservative substitutions are substitutions with similar amino acids within a group such as neutral, acidic, basic, and hydrophobic amino acids. Examples of substitutions within such groups would include gly, ala; val, ile, leu; asp, glu; asn, gln; ser, thr; lys, arg; phe, tyr; and nor, met. Additional amino acid substitutions, obtained by application of molecular modelling software to HLA allotyping database classification (DNA and serological), are shown:

| Group, 1 letter code | Group, 3-letter code |
| --- | --- |
| F, S | phe, ser |
| Q, R | gln, arg |
| K, N | lys, asn |
| E, G | glu, gly |
| G, R | gly, arg |
| H, Q | his, gln |
| I, T | ile, thr |
| V, A | val, ala |
| D, N | asp, asn |
| Y, F | tyr, phe |
| I, F | ile, phe |
| K, E | lys, glu |
| E, L, R | glu, leu, arg |
| Y, L | tyr, leu |
| S, V | ser, val |
| Y, N, F, D | tyr, asn, phe, asp |
| D, R | asp, arg |
| L, F | leu, phe |

In a preferred embodiment of the invention, amino acid modifications are made so as to substitute hydrophilic residues on the more hydrophilic end of the peptide of interest and hydrophobic residues on the more hydrophobic end of the peptide. Such substitutions result in the formation of an amphipathic helix with the desired epitope bracketed between the substitutions. Substituted amino acids in the D isomer can be employed to bracket epitopes to protect and stabilize the epitope and enhance immunogenicity of the epitope. Since D-amino acids are not cleaved by intracellular enzymes, such protion provides peptide epitopes of the desired length for interaction with MHC molecules when they are inserted at appropriate sites. This is described in detail in Example 8.5 below.

Usually, the modified sequence will not differ by more than about 20% from the sequence of at least one strain of the human immunodeficiency retrovirus except where additional amino acids are added at one or both termini for the purpose of providing an "arm" by which the peptide of this invention conveniently can be immobilized on solid phase supports, attached to macro molecules or modified to enhance immunogenicity by altering or enhancing MHC binding and presentation. The arms can comprise a single amino acid or as many as 50 or more amino acids, and typically are 1 to 10 amino acids, in length.

Amino acids such as tyrosine, cysteine, lysine, glutamic or aspartic acid, or the like can be introduced at the C- or N-terminus of the peptide or oligopeptide to provide for a useful functionality for linking. Cysteine is particularly preferred to facilitate covalent coupling to other peptides or to form polymers by oxidation.

Additionally, the peptide or oligopeptide sequences can differ from the natural sequence by the sequence being modified by terminal-$NH_2$ acylation (e.g., acetylation), thioglycolic acid amidation, or terminal carboxy amidation (e.g., with ammonia or methylamine), to provide stability, increased hydrophobicity for linking or binding to a support or other molecule, or for polymerization.

Thus, for example, in a preferred embodiment of the peptides disclosed herein, one or more cysteine residues or a combination of one or more cysteine residues with spacer amino acids can be added to the termini of the peptide. Glycine is a particularly preferred spacer when individual peptides are desired. When multiple peptide repeats of the peptide are desired, the peptide is synthesized off of a lysine core to form a tetravalent peptide repeat. The configuration is shown by way of example. Preferred peptides for use in oxidative polymerization are those in which at least two cysteine residues are added to the termini of a desired peptide. When two cysteine residues are present at the same end of the peptide, a preferred embodiment exists when the cysteine residues are separated by one to three spacer amino acid residues, preferably glycine. The presence of cysteine residues may allow the formation of dimers of the peptide and/or increase the hydrophobicity of the resulting peptide which facilitates immobilization of the peptide in solid phase or immobilized assay systems. Of particular interest is the use of the mercapto group of cysteines or thioglycolic acids used for acylating terminal amino groups or as the first amino acid for building multiple peptide repeats or the like for linking two of the peptides or oligopeptides or combinations thereof by a disulfide linkage or a longer linkage to form polymers that contain a number of epitopes. Such polymers have the advantage of increased immunological reaction. Where different peptides are desired for immunization, they are individually assembled and combined in a cocktail to provide the additional ability to induce antibodies that immunoreact with several antigenic determinants of different HIV isolates. To achieve the formation of antigenic polymers (synthetic multimers), compounds can be employed having bis-haloacetyl groups, nitroarylhalides, or the like, where the reagents are specific for these groups. The linking between the one or two mercapto groups of the peptides or oligopeptides can be a single bond or a linking group of at least 2 or more carbon atoms.

LINKING PEPTIDES TO MACROMOLECULAR CARRIERS

The subject peptide can be employed linked to a soluble macromolecular (e.g., not less than 5 kDal) carrier. Conveniently, the carrier can be a poly(amino acid), either naturally occurring or synthetic, to which antibodies are unlikely to be encountered in human serum. Examples of such carriers are poly-L-lysine, keyhole limpet hemocyanin, thyroglobulin, albumins, such as bovine serum albumin, tetanus toxoid, etc. The choice of the carrier is primarily dependent upon the ultimate use intended for the antigen and one of convenience and availability. In a preferred embodiment, the carrier comprises multiple repeats of glycopeptide a microparticle which can be synthesized or isolated from certain bacteria such as *Proprionibacterium acini* or the like. This microparticle is composed of muramyl dipeptide extensively crosslinked resulting in multimeric configurations.

When muramyl dipeptide is isolated from *Propionibacterium acini* or related organisms, strain selection is helpful, and selection is based on chemical analysis of the bacterial cell wall. The preferred embodiment is muramyl dipeptide extensively crosslinked with a dipeptide composed of L-alanine-D-isoglutamine.

From preliminary experiments, strain differences have been identified in which dipeptide composition and peptide length vary. Isolates with high concentrations of lipid A and O-acylated beta myristate are components of the cell wall. Preliminary experiments showed these differences are associated with increases in toxicity and decreases in adjuvant effect. Strain selection and the purification of the preferred embodiment is discussed by way of Example 4, below.

The MDP microparticle can be synthesized by employing procedures known in the art. It has been well established that MDP is a potent immunostimulant but has significant toxicity. Many attempts to reduce MDP toxicity have employed procedures to delay release, such as MDP incorporation into liposomes or other related compounds or modification of terminal groups. Chemical modification resulted in marked reduction in the desired adjuvant effect, and designs which change delivery rate have been difficult to control. By way of example, MDP microparticle configuration, size parameters, and antigen delivery attachment methods are provided below. Removal of lipids from the microparticle configuration facilitates rapid internalization of MDP by antigen presenting cells (APC). Antigen presenting cells are predominatly of monocytes lineage and include monocytes, macrophage, Histiocytes, Kuffer cells, Dendritic cells, Langerhans cells, etc. and participate in antigen processing and antigen presentation through MHC associated events. Factors which contribute to the development of immune responses to foreign protein can be, in part, determined by amino acid sequence and sequence susceptible to protease cleavage in the micro environment. Successful immune responses are most frequently observed to peptides which form an amphipathic helix with a hydrophobic terminus, preferably on the amino terminal end, and hydrophilic amino acids most frequently on the carboxyl terminal end. Sequence configurations that are resistant to protease degradation and form amphipathic helix arrangements are frequently strong immunogens. Residues which contain proline in the sequence are generally poorly immunogenic by preventing helix formation and glycosylation sites are less favorable and frequently inhibit responses directed at peptide epitopes. Antigen challenge which results in a successful immunological response in the host animal requires antigen processing and presentation of antigen through MHC associated events. Exogenous antigen is primarily processed by antigen presenting cells (APC) after internalization into endosomes. Following proteolysis by enzymes, such as cathepsin D, which are present and react in this acid environment, peptide fragments which satisfy the criteria described above are assembled with MHC class II and presented on the cell surface. When peptides are presented in sufficient density immune events result. The type of immune response is driven by the density of peptide per APC, micro-environment, the cytokine environment, and the lymphocyte type initially stimulated by antigen presenting cells. Following internalization, a cascade of cytokine responses is induced which modifies the micro-environment and establishes conditions conducive of immunological events.

By way of example, a unique MDP microparticle (0.01–0.2 micron) is used to deliver immunogen to antigen presenting cells resulting in immune responses to poorly immunogenic epitopes not observed using conventional methods as shown in Example 5 below. Quantitation of these immune responses demonstrate 10 to 100 fold increases in antibody concentration as compared to other adjuvants.

Subject peptides employed as immunogen can be linked to the carboxyl terminal amino acid moiety of muramyl dipeptide using either the amino or carboxyl terminus of the subject peptide or to the aldehyde oxidation product of the carbohydrate moiety as disclosed in the examples. There will be at least one molecule of the subject peptide per MDP microparticle, preferably 10–100 molecules of subject peptide per MDP microparticle and most preferably 100 to 1000 subject peptides per MDP microparticle. Carrier size and available linkage groups, therefore, will influence the number of subject peptides per carrier.

Macro-carrier composition affects immunogenicity by influencing preferential cell uptake, peptide half-life, and antigen presentation through MHC immunological events. One or more different subject peptides can be linked to the same macro-carrier but preferably a single subject peptide is attached either in the univalent or tetravalent configuration to the macro-carrier. When immunization with more than one subject peptide is desired, a cocktail of subject peptide macro-carrier conjugates can be prepared by mixing individual conjugates at ratios to optimize immunogenicity of each subject peptide introduced in the cocktail. In this configuration sufficient peptide is available on each macro-carrier conjugate (100–1000 peptides) to enhance antigen presentation by a single antigen presenting cell. Immunogenicity of the subject peptide will be optimized by adjusting both the number of subject peptides per macromolecular carrier, presentation configuration, such as amino versus carboxyl attachment, terminal amino acid modification, and space arm length and composition, as disclosed. In this configuration, antigen processing by the antigen presenting cell results in a high density, usually more than 100 and most frequently more than 500 peptides, presented at the cell surface of the antigen presenting cell through MHC interactions. With this configuration significantly higher concentrations of antibody are produced, following immunization, as shown in the examples below.

The manner of linking is conventional, employing such reagents as p-maleimidobenzoic acid, p-methyldithiobenzoic acid, maleic acid anhydride, succinic acid anhydride, glutaraldehyde, etc. The linkage can be made at the N-terminus, C-terminus, or at a site intermediate to the ends of the molecule. With multiple repeats of muramyl dipeptide, attachment of the subject peptide to aldehyde groups produced by the mild oxidation of sugar residues with, for example, sodium periodate following mild reduction with sodium borohydride and the like, the Schiff's base intermediate is converted to a stable covalent linkage. The number of peptides per microparticle can be controlled by varying oxidation conditions and quantitated by employing a radioactive tracer. These methods are well known in the art. The method of attachment and attachment configuration can vary from peptide to peptide as needed to achieve the desired response.

Various assay protocols familiar to those skilled in the art can be employed for detecting the presence of either antibodies to retroviral protein epitopes or detecting retroviral proteins in complex protein mixtures. Of particular interest is a novel assay herein disclosed in which the subject peptide is covalently attached to a detection label such as horseradish peroxidase and the native HIV protein expressing epitope or epitopes is either directly or indirectly attached to a solid phase support. In this configuration an antibody which recognizes the peptide epitope will bridge the epitope on the solid phase with the epitope on the label. With this method the epitope reactivity of an antibody to HIV can be determined and quantitated by varying the peptides attached to the label. Peptide epitopes which are associated with HIV serotype, virulence factors or other HIV characteristics can be identified and measured in any sample expressing these epitopes by a one step competitive immunoassay herein disclosed and provided by way of example.

Use of Antibodies and Their Respective Epitopes in Immunoaffinity Purification Procedures Antibodies specific for epitopes contained within HIV proteins and purified proteins containing these epitopes are of particular advantage for use in immunoaffinity purification of proteins and peptides containing these epitopes and antibodies reactive with them. Generally, the antibodies will have affinity association constants on the order of $10^8$ to $10^{12}$ M. Such antibodies can be used to purify proteins and peptides containing the epitopes of interest. Oftentimes, genetically modified bacteria can be used to make HIV proteins, and the recombinant fusion proteins of interest can be purified from the culture medium of the recombinant expression system if the expressed protein is secreted, or from the components of the disrupted biological expression system if it is not secreted, or from complex biological mixtures of proteins of which some or one component contains the epitope mimicking an epitope on HIV. Generally, the antibodies which are capable of reacting with HIV epitopes are attached to or immobilized on a substrate or support. The solution containing the epitopes then is contacted with the immobilized antibody under conditions suitable for the formation of immune complexes between the antibody and the protein containing the epitope. Unbound material is separated from the bound immune complexes, and the bound proteins are released from the immobilized antibody and recovered in the eluate.

Similarly, proteins or peptides containing epitopes of HIV or mimicking epitopes of HIV can be attached to or immobilized on a substrate or support and used to isolate antibodies of interest from a solution. A solution containing the antibodies, such as plasma from which albumin has been removed, is passed through a column of immobilized peptides or proteins containing the desired epitopes and, following immune complex formation, non-reactive antibody is separated from the bound immune complex and the antibody is released with an elution buffer and recovered in the eluate. This is of particular value in purifying protein containing epitopes mimicking epitopes of HIV but derived from sources phylogenetically unrelated to HIV.

Typically, antibodies are crudely purified from hyperimmune sera. Ascites fluid or cell culture supernatants and proteins or peptides containing epitopes mimicking HIV epitopes will be crudely purified from biological sources such as, but not limited to, body fluids, blood, blood components, cell extracts, tissue extracts of both adult and embryonic origins, and culture supernatants, extracts of cultured cells, venoms, and recombinant fusion products prior to attachment to a support. Such procedures are well known by those skilled in the art and may include fractionation with neutral salts at high concentration. Other purification methods, such as ion exchange chromatography, gel filtration chromatography, preparative gel electrophoresis, or affinity chromatography, also can be used to increase the purity of the preparation prior to its use as an immunoabsorbant. Affinity purified antibody can be prepared when desired by reacting crudely purified antibody preparations with a support matrix to which the reactive epitope or protein containing the epitope has been attached.

Of particular interest are antibodies to HIV epitopes phylogenetically mimicked through nature. Such antibodies are useful as therapeutic agents and also are useful for studying HIV by allowing purification of HIV proteins and the mapping of HIV proteins for sequence location and function. Such antibodies can be produced by immunization with HIV proteins/peptides derived from HIV and immunoaffinity purified by reacting the resultant hyperimmune polyclonal multivalent antisera with proteins/peptides derived from non-HIV sources such as embryonic proteins, venoms, and non-HIV microbial/viral components immobilized on a support as discussed above. The resulting immunoaffinity purified antibody is epitope specific for an epitope or epitopes shared by HIV and the phylogenetically unrelated protein used for its immunopurification. These epitope specific antibodies have particular utility in the immunoaffinity purification of proteins and peptides of both HIV and non-HIV origin. Such antibodies can be used to map the location of the epitope on HIV to determine its sequence, evaluate functional importance in the life cycle of HIV, its distribution within the clades of HIV and among other retroviridae, its association with HIV virulence, and, when non-toxic to man but neutralizing a crucial function in the life cycle of HIV, used to treat HIV infection.

The support to which the antibodies or epitopes are immobilized desirably has the following general characteristics: (a) weak interactions with proteins in general to minimize non-specific binding, (b) good flow characteristics which allow the flow through of high molecular weight materials, (c) possession of chemical groups that can be activated or modified to allow chemical linkage of the antibody or epitope, (d) physical and chemical stability in the conditions used to link the antibody, and (e) stability to the conditions and constituents of the buffers required for absorption and elution of the antigen. Some supports commonly used are agarose, derivatized polystyrenes, polysaccharides, polyacrylamide beads, activated cellulose, glass and the like. Various chemical methods exist for the attachment of antibodies and antigens to substrate supports. See generally, Cuatrecasas, P., *Advances in Enzymology* 36:29 (1972). The antibodies and antigens of the present invention can be attached directly to the support or, alternatively, through a linker or spacer arm. General conditions required for immobilization of antibody and antigens to chromatographic supports are well known in the art. See, for example, Tijssen, P., 1985, *Practice and Theory of Enzyme Immunoassay*, which is incorporated herein by reference. Actual coupling procedures will depend slightly on the characteristics and type of the antibody or the antigen to be coupled. Attachment typically occurs through covalent bonds.

An immune serum, ascites fluid or culture supernatant rich in antibody or extract or lysate of HIV virus, the supernatant or extract from a cultured biological expression system, the supernatant or extract from a suspension of the disrupted cells tissue or blood component (adult and embryonic) or other complex protein mixtures such as venoms, body fluids, or culture products containing the epitope then is added to the appropriate separation matrix. The mixture is incubated under conditions and for a time sufficient for antigen-antibody attachment to occur, usually at least 30 minutes, more usually 2 to 24 hours. The immobilized immune complexes containing the specifically bound antibody or epitopes then are separated from the complex mixture and extensively washed with absorption buffer to remove non-bound contaminants. The immune complexes then can be dissociated with an elution buffer compatible with the particular support, the attached protein, and the eluate protein. The elutable protein, antigen, or antibody is recovered in the eluate. Elution buffers and techniques are well known by those skilled in the art. Peptides that contain the epitope recognized by the antibody can be used in the elution buffer to compete for the antibody binding site and elutions can be performed under mild elution conditions. The selectively absorbed protein can be eluted from the affinity absorbent by altering the pH and/or ionic strength of the buffer or with chaotropic agents. The selection of an elution buffer, its concentration and other eluting conditions are dependent on the characteristics of the antibody-antigen interaction, and once determined should not be subject to significant change.

The eluted protein may require adjustment to a physiologic pH and ionic strength if low or high pH or ionic strength buffers or chaotrophic agents are used to dissociate the immune complex. Such adjustment can be made by dialysis or gel filtration chromatography. These methods also permit the eluted protein to regain its native conformation.

The foregoing methods yield, e.g., substantially purified proteins containing epitopes of, or mimicking epitopes of, HIV and antibodies reactive with the epitopes. The purified proteins typically will be greater than 50% pure, more usually at least 75% pure, and frequently greater than 95% to 99% pure.

Other features and advantages of the present invention will become apparent from the following experimental descriptions, which describe the invention by way of example. The examples further illustrate the process of this invention but are not meant to limit the invention in any way.

EXAMPLE 1

Preparation of Human Anti-HIV Antibody (IgG fraction) Pools for use in Mapping HIV Epitope Differences Between Man and Goat Immune Reactions Human sera from HIV-infected patients were obtained from a community health clinic with patient permission, patient signed informed consent, physician approval and local IRB approval. All sera were initially screened for HIV reactivity at a dilution of 1:10 employing a commercially available test kit from Abbott Laboratories. Sera with high reactivity (arbitrarily defined by test result absorbances greater than 1) were further evaluated by Western Blot analysis to identify those sera with antibody reactivities to most HIV proteins (env, gag and pol). Patient sera that demonstrated good reactivity to most HIV proteins as defined were further evaluated by microculture neutralization assays to identify the sera-containing antibody specifities which would neutralize HIV infectivity in microculture assays (total culturable infectious dose (TC1D) neutralization). Twenty-nine patients' sera with high antibody titer reactivity to gp160, gp120, p66/55, gp41, p24, and p17 and p10, and neutralized HIV infectivity in microculture were identified and pooled (20–40 ml each). Further evaluation of the pooled anti-human HIV revealed broad neutralization activity against multiple strains of HIV and high titer antibody (positive by Western Blot 1:100 or greater) to the nine epitope regions described in detail above. Human IgG was purified from this serum pool employing conventional procedures. Following purification the total IgG concentration was adjusted to 10 mg/ml, its composition and purity was evaluated by standard immunoassay procedures. The results demonstrated a purity of greater than 98% and a composition of human IgG. The purified human anti-HIV was divided into aliquots and frozen for subsequent use in experiments and procedures disclosed below. Those skilled in the art will be familiar with methods for characterizing both antigen and antibody pools to define specificities which may be used in subsequent determinations against unknown antibodies or antigens for comparative purposes.

As described in the following examples, this human anti-HIV was employed to follow the purification of HIV proteins from crude viral lysates and map HIV epitopes recognized by the human immune system and in competitive EIA to identify HIV epitopes targeted by antibodies produced in goats but not man. Western Blot analysis was employed to characterize antibody responses in goats immunized with either purified HIV proteins containing peptides of interest or synthetic versions of those peptides, and to evaluate the efficacy of a microparticle carrier complex designed to amplify immune responses to poorly immunogenic peptides. Antibodies which neutralized HIV infectivity were evaluated by a microculture procedure which employed purified human CD4 lymphocytes isolated from peripheral blood mononuclear cells (PBMC), employing standard techniques which use monoclonal antibody-conjugated magnetic particles to remove unwanted cells. CD4 lymphocytes were stimulated with mitogen to increase their susceptibility to HIV infection and were used throughout unless otherwise noted as the host target for HIV infection. $HIV1_{SF2}$ was employed throughout unless otherwise noted as the reference HIV strain. The effect of antibody on HIV infectivity was determined by microculture using techniques familiar to those skilled in the art. Infectivity is expressed as infectious units (IU). Antibody mediated reductions in IU were associated with neutralization of virus infectivity and expressed as change in infectious unit. The human anti-HIV pool was used throughout all experiments described herein that required human anti-HIV antibody. This human IgG anti-HIV pool was compared to several commercially available human anti-HIV preparations and had equal or greater HIV neutralizing activity and, when compared by Western Blot analysis, was significantly more reactive.

EXAMPLE 2

Characterization of Commercially Available HIV Viral Lysates Employed Herein

Preliminary Studies $HIV1_{MN}$, $HIV1_{BAL}$ and $HIV2_{NZ}$ were purchased from Advanced Bio-Technology, Inc., Columbia, Md., in the form of purified viral lysates. Analysis of these purified viral lysates demonstrated lot to lot variation in total protein content with a range of 0.8 mg/ml to 1.2 mg/ml. The protein composition of each HIV lysate was evaluated by SDS-PAGE and Western Blot analysis with human IgG anti-HIV. The HIV lysates were treated with protease inhibitors and nonionic detergents (1.0% v/v), such as Nonidet P-40 or Igepal CA630, to fully dissociate HIV proteins and glycoproteins into their monomeric forms, and clarified by filtration through a 0.22 micron filter. Lipids were removed with SeroClear employing standard procedures. It is well known to those skilled in the art that HIV incorporates human proteins into its envelope as part of the budding process. Such contaminants once identified were removed by immunoaffinity chromatography. In the initial purification step serum contaminants present in growth media added to facilitate cell growth and contaminants in the HIV lysate were removed by immunoaffinity chromatography employing anti-normal human serum Sepharose CL6B (2–3 mg antibody/gram Sepharose). Chromatography of HIV lysates were conducted at a matrix to lysate ratio of 1:1 volume/volume at a flow rate of 10 ml/hour. The chromatography and elution were monitored spectrophotometrically at a wave length of 280 nm. The protein rich non-binding fraction containing the HIV related proteins was concentrated to 1 mg protein/ml and stored at −70° C. for future use as needed. Proteins bound by the affinity matrices were eluted with glycine-HCl buffer pH 2.2 in 0.9% NaCl. Eluates were neutralized, dialyzed in PBS pH 7.8 containing 0.1% Igepal CA630, concentrated and stored at −70° C. for future analysis. SDS-PAGE with Western Blot analysis of purified HIV preparations consistently demonstrated the presence of gp160, gp120, p66/55, gp41, p10, p24, p17 and p7, employing human anti-HIV IgG. HIV proteins were not detected in glycine HCl eluate employing Western Blot analysis, but SDS-PAGE gels stained with coomassie brilliant blue for protein visualization demonstrated 2–3 weakly stained bands.

Characterization of Anti-HIV Antibody Produced to Partially Purified HIV Lysates Goats (n=2) were immunized with the purified HIV proteins obtained above and responded immunologically with antibodies which reacted with immunodominant epitopes on HIV. Further evaluation of this antiserum demonstrated the presence of cytotoxic antibodies which reacted with both HIV-infected and non-infected $CD4^+$ lymphocytes, and red blood cell (RBC) agglutinins were detected. These agglutinins were reacted with all human RBC blood groups and RBC's from rabbits and guinea pigs. Two possibilities for these unwanted antibody specificities were considered. One possibility was contamination from HIV lysates with proteins of cell culture origin, and the second was mimicry between HIV proteins/glycoproteins and glycoproteins found in man and other animal species. It is well known that host membrane proteins are often identified in the envelope of HIV. The incorporation of host membrane components into the envelope of HIV is thought to be non-specific and associated with the budding of the mature virion. Two such proteins previously identified in mature virion envelope are human HLA class I and class II antigens. Both HLA class I and class II antigens were quantitated employing an enzyme linked immunoassay and results demonstrated the presence of both HLA class I and class II antigens in these HIV preparations and at concentrations disproportionate to their concentration measured in cell membrane preparations derived from uninfected culture cells. Further studies confirmed the presence of HLA class I and class II antigens in different preparations (n=17) of HIV viral lysate. The measured concentration in these preparations was variable but consistently 10 to 100 times greater than that measured in membrane extracts from uninfected control cells. The goat anti-HIV antibody was tested by Western Blot Analysis against known HLA class I and class II isolates and confirmed to contain antibody specificities directed against HLA class I, HLA class II (alpha and beta chain) and beta 2 microglobulin. This antibody was evaluated for HLA allotype specificity. Commercial trays containing lymphocytes of known allotypes were employed as targets. Under assay conditions, this antibody was cytotoxic to all lymphocytes, and this cytotoxicity was partially inhibited with soluble HLA class I and HLA class II in a dose dependent manner. (Table 2.1).

TABLE 2.1

HLA Class I Inhibition of Lymphocytotoxicity in Antiserum Produced to Purified HIV Lysates

| Dilution | Anti-HIV | Anti-HIV & HLAI & II 25 ug | Anti-HIV & HLAI & II 50 ug | Anti-HIV & HLAI & II 100 ug | Anti-HIV & HLAI & II 200 ug | Pre-Immune Serum |
| --- | --- | --- | --- | --- | --- | --- |
| u | 8 | 8 | 8 | 8 | 8 | 0 |
| 1:5 | 8 | 8 | 8 | 8 | 8 | 0 |
| 1:10 | 8 | 8 | 4 | 4 | 4 | 0 |
| 1:20 | 8 | 8 | 4 | 4 | 4 | 0 |
| 1:40 | 8 | 8 | 4 | 4 | 4 | 0 |
| 1:80 | 8 | 4 | 2 | 4 | 2 | 0 |
| 1:160 | 8 | 4 | 0 | 2 | 0 | 0 |

TABLE 2.1-continued

HLA Class I Inhibition of Lymphocytotoxicity in Antiserum Produced to Purified HIV Lysates

| Dilution | Anti-HIV | Anti-HIV & HLAI & II 25 ug | Anti-HIV & HLAI & II 50 ug | Anti-HIV & HLAI & II 100 ug | Anti-HIV & HLAI & II 200 ug | Pre-Immune Serum |
|---|---|---|---|---|---|---|
| 1:320  | 8 | 2 | 0 | 0 | 0 | 0 |
| 1:640  | 8 | 0 | 0 | 0 | 0 | 0 |
| 1:1280 | 4 | 0 | 0 | 0 | 0 | 0 |

Soluble HLA class I & II was added to micro titer wells containing anti HIV antibody and incubated overnight at 4° C. Soluble HLA I & II reduced lymphocytotoxicity but had no additional effect at concentrations above 50 ug.

Further studies demonstrated an antibody that reacted with a phylogenetically preserved carbohydrate antigen present on gp120, human red and white blood cells, and red blood cells from different animals including rabbit, rat, and guinea pig. Absorption studies with human and rabbit red cells completely removed the remaining antibody activity to both RBC's (Table 2.2) and lymphocytes (Table 2.3) following absorption with S-HLA-I & II.

TABLE 2.2

Analysis of Anti RBC Absorbed Anti-HIV Antibody for RBC Agglutinins Cells

| RBC Absorp- | Anti* HIV1 | | | Anti* HIV2 | | | Anti* HIV1 & 2 | | |
|---|---|---|---|---|---|---|---|---|---|
| tion # | AB+ | 0+ | rabbit | AB+ | 0+ | rabbit | AB+ | 0+ | rabbit |
| 0 | 256 | 256 | 256 | 256 | 128 | 128 | 128 | 256 | 128 |
| 1 | 128 | 128 | 128 | 128 | 64  | 128 | 64  | 128 | 128 |
| 2 | 32  | 32  | 32  | 32  | 32  | 64  | 32  | 32  | 32  |
| 3 | 8   | 4   | 4   | 4   | 4   | 4   | 8   | 4   | 4   |
| 4 | 2   | —   | —   | —   | —   | —   | 2   | —   | —   |

*Antisera produced to purified HIV lysate resulted in RBC agglutinins produced in goats following immunization. Goats (n = 2 each) were immunized with HIV1$_{MN}$ and HIV1$_{BAL}$ andor HIV2$_{NZ}$, respectively.

TABLE 2.3

Analysis of Anti RBC Absorbed Anti-HIV Antibody for Lymphocytotoxicity During Immunization

| RBC Absorp- tion | Anti* HIV1 | | | Anti* HIV2 | | | Anti* HIV1 & 2 | | |
|---|---|---|---|---|---|---|---|---|---|
| (n) # | AB+ | 0+ | rabbit | AB+ | 0+ | rabbit | AB+ | 0+ | rabbit |
| 0 | 512 | 512 | 256 | 1024 | 1024 | 1024 | 512 | 1024 | 1024 |
| 1 | 256 | 256 | 256 | 256  | 512  | 512  | 256 | 256  | 256  |
| 2 | 128 | 64  | 128 | 64   | 64   | 128  | 64  | 128  | 64   |
| 3 | 32  | 16  | 16  | 16   | 16   | 32   | 16  | 16   | 16   |
| 4 | 4   | 4   | 4   | 4    | 4    | 4    | 4   | 4    | 4    |
| 5 | 2   | 2   | 2   | ±    | 2    | 2    | 2   | 2    | 2    |

*Antisera produced to HIV without glycosidase treatment at 20 week blood collection date and absorbed 0–5 times with red blood cells and tested against lymphocytes for lymphocytotoxicity.

Following the absorption and removal of antibody specificities to HLA and hemoagglutinins the goat anti-HIV antibody was identified to contain specificities similar to those previously described in the literature. This information demonstrated the need for modification of the HIV proteins to remove carbohydrate and HLA antigens to avoid the generation of cytotoxic antibodies directed against human antigens.

EXAMPLE 3

Purification and HLA Class I and Class II Antigen Removal and Carbohydrate Removal of HIV Protein Isolated from HIV Lysates HIV lysates of HIV1$_{MN}$, HIV1$_{BAL}$ and HIV2$_{NZ}$ were purchased from Advanced Biotechnologies, Columbia, Md. They contained protein concentrations in the range 0.8–1.2 mg protein/ml. Protease inhibitors were added to protect the proteins from degradation, and non-ionic detergent (Igepal Ca-630, or Nonidet P-40) was added to dissociate HIV proteins. The mixture was dispensed into capped extraction tubes with a delipidating reagent to remove lipids and clarify the mixture. Lipids were differentially dissolved in the organic layer after centrifugation and the aqueous phase was removed.

Contaminants of cell culture origin, including HLA, were removed by immunoaffinity chromatography on five separate affinity matrices prepared by the covalent attachment of: immunoaffinity purified polyclonal IgG antibodies to human serum proteins, monoclonal IgG antibody to HLA-1, monoclonal IgG antibody to HLA-2, monoclonal antibody to β2-microglobulin, immunoaffinity purified polyclonal IgG antibodies to lymphocyte and red blood cell membrane antigens. Each matrix contained 2–3 mg antibody per g Sepharose CL6B. Columns were configured in a tandem arrangement, and matrices were poured and equilibrated with PBS at pH 7.8 containing 0.1% Igepal Ca-630. Lysate solutions in volume equivalent to column bed volume were successively chromatographed through each column at a flowrate of 10 ml/h. The chromatography and elution were monitored spectrophotometrically at a wavelength of 280 nm. The protein-rich non-binding fraction containing the HIV related proteins were concentrated to 1 mg protein/ml.

SDS was added to the immunoaffinity-purified mixture containing the HIV proteins of interest and the mixture was heated at 70° C. for 10 minutes. The protein were enzymatically deglycosylated using PGNase. The protein mixture was fractionated by size chromatography on Sepharose G50 pre-equilibrated with saline containing 0.1% non-ionic detergent. Protein fractions were collected and those containing the desired HIV proteins were individually pooled. The three protein pools, individually enriched for gp160 and gp120, p66/55 and gp41, and p24, p17 and p10 were retained. Fractions were stored at −70° C. until further processing.

Detailed methods for quantitation and removal of human leukocyte antigen (HLA) are disclosed in "Identification, Characterisation, and Quantitation of Soluble HLA Antigens in Circulation and Peritoneal Dialysate of Renal Patients", F. Gelder, *Annals of Surgery* Vol. 213, (1991), incorporated herein by reference.

Table 3.1 shows data obtained from the purification.

TABLE 3.1

Purification of HIV Lysate

| Fractionation Step | Protein mg/ml | Volume ml | Total Protein | HLA I ng/ml | HLA II ng/ml | % Recovery |
|---|---|---|---|---|---|---|
| HIV Lysate | 1.13 | 10   | 11.3 | 1833 | 692  | 100% |
| Post Lipid Removal | 0.96 | 10.3 | 9.8  | 1726 | 683  | 86.7 |
| Post Affinity Chromatography | 0.44 | 19.5 | 8.58 | <10  | <10  | 75.9 |

TABLE 3.1-continued

Purification of HIV Lysate

| Fractionation Step | Protein mg/ml | Volume ml | Total Protein | HLA I ng/ml | HLA II ng/ml | % Recovery |
|---|---|---|---|---|---|---|
| Post Concentration | 1.01 | 8.1 | 8.18 | <10 | <10 | 72.3 |

HIV preparations purified as described typically were devoid of contaminants, including HLA class I or class II. SDS-PAGE with Western Blot analysis of purified HIV preparations consistently demonstrated the and p7 employing the pooled human IgG anti HIV.

EXAMPLE 4

Preparation and Characterization of the Biochemical and Conformational Requirements of MDP Microparticle for Eliciting Adjuvant Effects with Purified HIV A multiple repeat of muramyl dipeptide (MDP) isolated from *Propionibacterium acini*, formed the core structure of the MDP microcarrier complex of this example. The chemical composition of the monomeric subunit is

[Structure: MDP sugar ring with OH, O, OH, NHAc, HO substituents]

$CH_3CHO-NHCH(CH_3)CO-NHCH(CH_2CH_2-COOH)CONH_2$

MDP has well known immunostimulatory properties which have been extensively evaluated in studies designed to determine its effect on increasing immune function. Those skilled in the art are familiar with this effect.

To date, both MDP isolated from natural sources and synthetic MDP have been associated with significant toxicity when administered to mammals. This toxicity has limited the effectiveness of MDP as a carrier.

A method for the isolation of MDP free from toxic components is provided herein. *Propionibacterium acini* was grown to a mid-stationary growth phase and washed to remove contaminants of bacterial culture origin employing techniques well known to those in the art. Hydrophobic components contained in the cell walls and cytoplasm were sequentially extracted by successive washes in gradual concentrations of ethanol/methanol/water at elevated temperatures. The resulting MDP microparticle was suspended in 10% ethanol and its concentration was measured by relating its absorbance at 540 nm to the absorbance of turbidity standards. The concentration of the MDP microparticle was adjusted to 1 mg/ml for storage and later use.

Analysis of this preparation demonstrated muramyl dipeptide extensively crosslinked with a microparticle size of 0.1 to 0.2 micron. The terminal dipeptide amino-linked L-alanine-D-isoglutamine was identical to the monomeric structure shown above. It is well known that there can be differences between bacterial strains and these differences can result in differences in peptide composition, such as terminal peptides with five or more amino acids, changes in dipeptide amino acid composition, in particular L-alanine-L-isoglutamine, and sites where O-acylated beta myristate groups have been incorporated. These are not desirable and account for toxicity and poor adjuvant properties of MDP isolated from natural sources. In a preferred embodiment, the MDP microparticles (0.01–0.2 micron; preferrably 0.05–0.1) have amino-linked L-alanine-D-isoglutamine dipeptide. Such a microparticle can be isolated from natural sources, as above, or synthesized using well known synthetic procedures.

EXAMPLE 5

Preparation and Preliminary Evaluation of MDP-Immunogen Conjugate

The adjuvant effect of the MDP microparticle (0.2 u) of the preceding example on antibody production was evaluated employing a poorly immunogenic monoclonal human lambda light chain fragment lacking approximately 22 amino acids at the sulfhydryl bridge (Mr ~18,000) as the immunogen (I). Two conjugates were made, one in which the immunogen was covalently conjugated to MDP through the carboxyl terminal group and one wherein conjugation was through the amino terminal group. MDP-immunogen conjugates were assembled in a stepwise manner and reagent exchange was performed after each step by centrifugation, supernatant removal and replacement with the required reagent to continue the conjugation sequentially through MDP:immunogen assembly. The molar ratios that are shown with each reaction and the reagent exchange that was performed after each step prevented multiple point attachment of the immunogen which, from preliminary experiments, significantly reduced immune antibody responses.

Synthesis of $MDP:NH_2:Immunogen:CO_2H$

Protocol for Efficient Two-Step Coupling of HIV Proteins to Muramyl Dipeptide Using EDC The following procedure, adapted from a procedure described by Grabarek, Z. and Gergely, J., *J. Anal. Biochem.* 185:1311 (1990), allows for sequential coupling of HIV proteins and peptides to MDP without exposing the HIV protein to 1-ethyl-3-(3-dimethylaminopropyl)carbodiimide (EDC) and thus affecting carboxyls on HIV. This procedure calls for quenching the first reaction with a thiol compound. The reaction is carried out in 2-[N-morpholino]ethane sulfonic acid (MES) (pH 4.5–5.0).

MDP (10 mg) lyophilized from water resuspended in MES (0.5 ml) (pH 4.5–5.0) and 0.5 ml EDC (0.5 mg~2 mM) dissolved in MES (pH 4.5–5.0) were combined and reacted for 15 minutes at room temperature. 2-mercaptoethanol (final concentration of 20 mM) was added to quench the EDC and separated by centrifugation. The reaction mixture was washed once with MES and resuspended in 0.5 ml MES (pH 4.5–5.0). The human λ light chain fragment dissolved in MES was added to the activated MDP at a molar ratio of about 2:1. The PH of the reaction was slowly increased over a 15 minute period to 8.5 by the addition of MES (0.5M pH 8.5) and reacted for 2 hours at room temperature. The concentration of the λ light chain fragment added to MDP was calculated from quantitative analysis of MDP terminal $CO_2H$ group and expressed as mole $CO_2H$ per mg MDP. The reaction was quenched by adding hydroxylamine to a final concentration of 10 mM. This method of quenching hydrolyzed any unreacted MDP activation sites and resulted in regeneration of the original carboxyls. Other means of quenching involve adding 20–50 mM Tris, lysine, glycine, or ethanolamine; however, these primary amine-containing compounds will result in modified carboxyls MDP. When the MDP is used with an HIV synthetic peptide and modification of that peptide is desired, such as to change hydrophobicity or to attach bio-active compounds, the modification can be attained by adding the desired compound prior to the final quench step. This permits the desired compounds to be added sequentially following the initial coupling with HIV peptides. Bioactive peptides also could be added at desired ratios with HIV peptides as a single step when greater control of peptide immunogenicity is desired. Biological response modifiers such as IL2 are well known to those skilled in the art and could be used for this purpose.

Separation was achieved by centrifugation, a wash step, and resuspension in the buffer of choice.

PREPARATION OF MDP-CO$_2$H-IMMUNOGEN-NH$_2$

Synthesis of MDP:NH$_2$CH$_2$CH$_2$NH$_2$:CO$_2$H:Immunogen:NH$_2$

Protocol for Efficient Three-Step Coupling of Proteins to Muramyl Dipeptide Using EDC This procedure allows for sequential coupling of a protein or peptides to MDP without exposing the protein to EDC and thus affecting amino groups on the protein. The procedure employs two intermediate steps conducted sequentially. The initial reaction is carried out in MES (pH 4.5–5.0). MDP (10 mg) lyophilized from water resuspended in 0.5 ml MES pH4.5 and 0.5 ml EDC (0.5 mg~2 mM) dissolved in MES were combined and reacted for 15 minutes at room temperature. Excess EDC was quenched by the addition of 2-mercaptoethanol (final concentration of 20 mM), and the activated MDP was separated by centrifugation, washed two times with MES and resuspended in 0.5 ml MES (pH 4.5). Diaminoethane (NH$_2$CH$_2$CH$_2$NH$_2$), dissolved in MES (pH4.5) was added to the activated MDP at a molar ratio of about 10:1. The pH was slowly increased over a 15 minute period by the addition of MES 0.5M pH8.5 and reacted for 1 hour at room temperature. MDP:NH$_2$CH$_2$CH$_2$NH$_2$ was separated by centrifugation, washed two times with MES and resuspended in 0.5 ml MES pH 4.5. The λ light chain fragment was suspended in 0.5 ml MES pH4.5, and 0.5 ml EDC (0.5 mg~2 mM) dissolved in MES was added and reacted for 15 minutes at room temperature. Excess EDC was quenched by the addition of 2-mercaptoethanol (final concentration of 20 mM) and the activated protein was separated from excess reducing agents and inactivated crosslinkers by size chromatography on an appropriate size gel filtration column. The activated protein was added to the activated MDP:NH$_2$CH$_2$CH$_2$NH$_2$ at a molar ratio of about 5:1 and reacted for 2 hours at room temperature. The concentration of protein added to MDP was calculated from quantitative analysis of MDP terminal CO$_2$H group and expressed as mole CO$_2$H per mg MDP. The reaction was quenched by adding hydroxylamine to a final concentration of 10 mM. This method of quenching hydrolyzed any unreacted MDP activation sites and resulted in regeneration of the original carboxyls. If an HIV synthetic peptide is used as the immunogen and modification of that peptide is desired, such as to change hydrophobicity of that peptide or attach bioactive compounds, the modification can be accomplished as described above. Separation was achieved by centrifugation, a wash step, and resuspension in the buffer of choice.

It should be noted that bioactive compounds may require the intermediate step described above when attachment through the CO$_2$H group is desired.

EXAMPLE 6

Comparative Study of MDP Immunogen Conjugate Against Commercial Adjuvants Including Freunds Complete Adjuvant, RIBI®, Titer Max® and Alum The adjuvant effect of this MDP microparticle (0.1 u) on antibody production was evaluated employing the poorly immunogenic monoclonal human lambda light chain fragment described in the preceding example (Mr ~18,000) as the immunogen (I). Two conjugates were prepared, one in which the immunogen was covalently conjugated to MDP through the carboxyl terminal group and one wherein the conjugation was through the amino terminal group.

Rabbits (n=5 each group) were immunized subcutaneously with approximately 100 micrograms of lambda light chain attached to 500 microgram MDP and emulsified in squalene. Animals were immunized at monthly intervals and test bleeds were obtained prior to immunization and at two week intervals throughout. The antibody responses to MDP:NH$_2$—I—CO$_2$H and MDP:NH$_2$CH$_2$CH$_2$NH$_2$:HO$_2$C—I—NH$_2$ were comparable in activity; however, the MDP:NH2—I—CO$_2$H-stimulated rabbits produced at least one additional antibody specificity determined by competitive EIA. The antibody responses obtained were compared to those obtained when conventional adjuvants were employed for antibody response, including Freund's complete adjuvant, Ribi®, Titer Max® and Alum (aluminum hydroxide). Both MDP:HO$_2$C—I—NH$_2$ and MDP: NH$_2$—I—CO$_2$H were significantly superior to the conventional adjuvants with immunogen in inducing antibody. Immunogen concentration (100 ug/immunization) and immunization schedule were identical in all groups. Table 6.1 shows the antibody titer measured at bi-weekly intervals and titer is expressed as the reciprocal of the dilution producing a positive reaction as described above. Both MDP conjugates were superior to conventional and well known adjuvants.

TABLE 6.1

| Week | *MDP:I CO$_2$H | +MDP:I NH$_2$ | Freund's Complete | Ribi | Titer Max | Alum |
|---|---|---|---|---|---|---|
| T-0 | — | — | — | — | — | — |
| 2 | — | — | — | — | — | — |
| 4 | 2 | — | — | — | — | — |
| 6 | 16 | 4 | — | — | — | — |
| 8 | 256 | 128 | — | — | — | — |
| 10 | 512 | 512 | 4 | 4 | 4 | — |
| 12 | 1024 | 512 | 16 | 16 | 16 | — |
| 14 | 4096 | 2048 | 32 | 32 | 64 | 4 |
| 16 | 4096 | 4096 | 64 | 128 | 256 | 8 |
| 18 | 8192 | 4096 | 256 | 512 | 1024 | 32 |
| 20 | 16384 | 8192 | 256 | 512 | 2048 | 32 |

T-0 = Primary immunization and pre-immunization blood collection.
MDP-I muramyl dipeptide:immunogen micro particle (≦0.2u).
*Peptide was conjugated at amino terminal group to isoglutamine with carboxy terminus exposed. (MDP:I:CO$_2$H) + Peptide was conjugated at carboxy through an intermediate step employing diaminoethane to modify the carboxyl terminus of MDP. (MDP:I:NH$_2$)

EXAMPLE 7

Cytokine Response of Peripheral Blood Mononuclear Cells Induced with MDP:NH$_2$: I:CO$_2$H and MDP:NH$_2$CH$_2$CH$_2$NH$_2$:O$_2$HC—I—NH$_2$ Immunogens To further evaluate the mechanisms associated with the increased antibody response to the MDP microparticle-immunogen complexes, an in vitro method which measured cytokine production of peripheral blood mononuclear cells was employed and compared to known cytokine inducers. Lipopolysaccharide (LPS) and LPS with phytohemagglutinin (PHA) were employed as known cytokine inducers. Cytokines were quantitated employing a well-established assay and expressed as units/ml. Peripheral blood mononuclear cells were isolated by Ficol Hypaque gradient centrifugation and adjusted to a concentration of $2 \times 10^6$/ml in tissue culture media. Cells (100 ul) were plated into microculture wells. MDP:I:$CO_2$H, MDP:I:$NH_2$, PHA+LPS, LPS and media alone were added undiluted or diluted 1:10 and 1:25 (10 ul). Cultures were incubated at 37° C. in a 5% $CO_2$ atmosphere for 48 hours and supernatants were removed and assayed by standard bioassays and/or EIA methods.

TABLE 7.1

|  | IFNR | IL2 | TNF | IL6 |
|---|---|---|---|---|
| MDP:I:$CO_2$H | 550 | 510 | 152 | 62 |
| MDP:I:$NH_2$ | 520 | 495 | 176 | 73 |
| LPS + PHA | 340 | 320 | 495 | 450 |
| LPS | 210 | 150 | 325 | 310 |
| MEDIA | 0 | 0 | 0 | 0 |
| I:$CO_2$H | 496 | 398 | 68 | 25 |
| $NH_2$ | 23 | 410 | 72 | 21 |
| LPS + PHA | 205 | 165 | 210 | 152 |
| LPS | 175 | 90 | 135 | 140 |
| I:$CO_2$H | 125 | 90 | 5 | 10 |
| I:$NH_2$ | 51 | 85 | 9 | 10 |
| LPS + PHA | 20 | 10 | 15 | 20 |
| LPS | 20 | 10 | 15 | 20 |

Both MDP:I:$CO_2$H and MDP:I:$NH_2$ stimulated greater Type I cytokine responses than LPS + PHA or LPS alone. Type 1 cytokine responses enhanced immune events while Type 2 cytokine response is indicated by elevated IFN gamma and IL2 and lower levels of TNF and IL6.

to remove carbohydrate and all preparations (with and without carbohydate) were purified as above. An aliquot of each was conjugated to MDP through the amino terminal residue in accordance with the procedures set forth in Example 5, and individually suspended in squalene. For comparison, these HIV proteins also were emulsified in Freund's complete adjuvant without conjugation to MDP.

Group 1—$HIV1_{MN}$: $HIV1_{BAL}$, 1:1, without carbohydrate removal;

Group 2—$HIV1_{MN}$: $HIV1_{BAL}$, 1:1, with carbohydrate removal;

Group 3—$HIV2_{NZ}$ without carbohydrate removal;

Group 4—$HIV2_{NZ}$, with carbohydrate removal

Group 5—$HIV1_{MN}$: $HIV1_{BAL}$: $HIV2_{NZ}$, 1:1:1, without carbohydrate removal;

Group 6—$HIV1_{MN}$: $HIV1_{BAL}$: $HIV2_{NZ}$, 1:1:1, with carbohydrate removal;

Group 7—$HIV1_{MN}$: $HIV1_{BAL}$, $HIV2_{NZ}$, 1:1:1, without carbohydrate removal and emulsified in Freund's complete adjuvant without conjugation to MDP.

Group 8—$HIV1_{MN}$: $HIV1_{BAL}$: $HIV2_{NZ}$, 1:1:1, with carbohydrate removal and emulsified in Freund's complete adjuvant without conjugation to MDP.

Goats were stratified into immunization groups 1–8 (n=3 each) and respectively immunized at the intervals shown in Table 8.1 with 100 ug HIV/immunization. Blood samples were obtained prior to immunization and at biweekly intervals. Antibody reactivity was quantitated by EIA using the FDA approved commercially available test kit from Abbott Laboratories. Results were expressed as the reciprocal of the antisera dilution that produce an absorbance value >1.0.

TABLE 8.1

Analysis of Anti HIV Antibody Response to HIV Proteins

| Week # | Group 1 Anti HIV1 | Group 2 Anti HIV1[1] | Group 3 Anti HIV2 | Group 4 Anti HIV2[2] | Group 5 Anti HIV1&2 | Group 6 Anti HIV1&2[1] | Group 7 Anti HIV1&2 | Group 8 Anti HIV1&2 |
|---|---|---|---|---|---|---|---|---|
| T-O* | 0 | 0 | 0 | 0 | 0 | 0 | 0 | 0 |
| 2 | 0 | 0 | 0 | 0 | 0 | 0 | 0 | 0 |
| 4* | 8 | 8 | 8 | 4 | 8 | 8 | 0 | 0 |
| 6 | 64 | 64 | 32 | 16 | 64 | 128 | 2 | 0 |
| 8* | 64 | 128 | 32 | 32 | 64 | 128 | 4 | 2 |
| 10 | 512 | 512 | 64 | 128 | 256 | 512 | 16 | 8 |
| 12* | 512 | 1024 | 128 | 256 | 512 | 1024 | 16 | 16 |
| 14 | 2048 | 2048 | 512 | 512 | 1024 | 2048 | 32 | 32 |
| 16* | 4096 | 4096 | 256 | 512 | 4096 | 4096 | 64 | 32 |
| 18 | 4096 | 8192 | 512 | 1024 | 8192 | 8192 | 128 | 54 |
| 20 | 8192 | 16384 | 1024 | 1024 | 16384 | 16384 | 128 | 64 |

T-O = Primary immunization and pre-immunization blood collection
[1] - Carbohydrates removed
* - Immunization & Booster

EXAMPLE 8

Characterization of the Antibody Response in Goats to HIV Proteins Untreated and Treated to Remove Carbohydrates Moieties and Comparison of the Adjuvant Properties of MDP Microparticles with Conventional Adjuvants

EXAMPLE 8.1

$HIV1_{MN}$, $HIV1_{BAL}$ and $HIV2_{NZ}$ viral lysates were purchased from Advanced Biotechnologies Inc., Columbia, Md. and one-half of each preparation was treated enzymatically The antibody responses were measured at bi-weekly intervals throughout immunization. There was no significant difference in antibody reactivity, measured by EIA, between individual animal groups (Groups 1&2, 3&4, 5&6) with MDP. Carbohydrate removal had no effect on production of antibody to the desired anti-HIV proteins.

EXAMPLE 8.2

Antisera obtained as described in Example 8.1 were evaluated for hemagglutinating antibodies. As can be seen from Table 8.2, carbohydrate removal from the HIV proteins obliterated the hemagglutination response.

TABLE 8.2

Analysis of Anti HIV Antibody Response to Red Blood Cells

| Week # | Group 1 Anti HIV1 | Group 2 Anti HIV1[1] | Group 3 Anti HIV2 | Group 4 Anti HIV2[2] | Group 5 Anti HIV1&2 | Group 6 Anti HIV1&2[1] | Group 7 Anti HIV1&2 | Group 8 Anti HIV1&2[1] |
|---|---|---|---|---|---|---|---|---|
| T-O* | — | — | — | — | — | — | — | — |
| 2 | — | — | — | — | — | — | — | — |
| 4* | — | — | — | — | — | — | — | — |
| 6 | 2 | — | 2 | — | 4 | — | 4 | — |
| 8* | 4 | — | 4 | — | 4 | — | 8 | — |
| 10 | 16 | — | 8 | — | 8 | — | 16 | — |
| 12* | 32 | — | 8 | — | 32 | — | 16 | — |
| 14 | 64 | — | 64 | — | 128 | — | 64 | — |
| 16* | 64 | — | 64 | — | 64 | — | 128 | — |
| 18 | 128 | — | 128 | — | 128 | — | 256 | — |
| 20 | 256 | — | 256 | — | 128 | — | 256 | — |

T-O = Primary immunization and pre-immunization blood collection
[1] - Carbohydrates removed
* - Immunization & Booster HIV preparations treated to remove carbohydrate groups failed to produce antibody reactivities able to agglutinate red blood cells (Table 8.2A). Goats immunized with MDP-HIV conjugates without carbohydrate depletion and a goat immunized with purified HIV without carbohydrate depletion emulsified in Freund's complete adjuvant produced red cell agglutinins. There was no detectable difference in the titer of red cell agglutinins in antisera from goats immunized with MDP-HIV conjugates or HIV emulsified in Freund's complete adjuvant. The red cell agglutinins described herein were essentially identical to those described in the preliminary studies of Example 2. These agglutinins were cytotoxic (Table 8.2A). However, there was no detectable antibody reactivity to HLA class I or class II and absorption with red blood cells completely removed both the hemagglutinating and the cytotoxic antibody reactivity.

To evaluate the possibility of mimicry between HIV and RBC carbohydrate groups, additional antisera were produced by immunizing a goat with an immunogen composed of purified and pooled cell membranes isolated from human red blood cells. Western Blot analysis employing this antisera demonstrated reactivity with a red blood cell glycoprotein (~Mr35,000) and reacted with HIV gp41 and gp120. However, HIV gp41 and gp120 treated to remove carbohydrate groups were unreactive. These data were consistent with phylogenetic mimicry between carbohydrate epitope on HIV and red blood cell glycoproteins.

Western Blot analysis demonstrated strong reactivity to most HIV proteins, including gp160, gp120, gp41, p66/55, p10, p24, p17 and p7. There was no apparent difference in the reactivity or specificity of these antibodies to the HIV epitopes disclosed herein. These antibodies reacted to all HIV isolates tested, including those which have been shown to have resistance to reverse transcriptase and protease inhibitors.

EXAMPLE 8.3

Neutralization of HIV Infectivity by Antibodies produced to Carbohydrate-Depleted HIV This example describes and characterizes the neutralization of HIV infectivity using the antibodies produced to carbohydrate depleted HIV disclosed above. The results indicate that these antibodies contain high levels of neutralizing activity and protect CEM cells from infection in a dose dependent manner.

Neutralization Assay:

A sensitive neutralization assay was employed to quantitate the effect of goat anti HIV on HIV infectivity. The CEM CD4+ cell line, which is highly susceptible to HIV infection, was chosen as the target cell to determine the effect of this antibody on HIV infectivity. The antibody and dilutions

TABLE 8.2A

Sequential Analysis of Anti HIV Antibodies for Lymphocytotoxicity

| Week # | Group 1 Anti HIV1 | Group 2 Anti HIV1[1] | Group 3 Anti HIV2 | Group 4 Anti HIV2[2] | Group 5 Anti HIV1&2 | Group 6 Anti HIV1&2[1] | Group 7 Anti HIV1&2 | Group 8 Anti HIV1&2[1] |
|---|---|---|---|---|---|---|---|---|
| T-O* | ± | ± | ± | ± | ± | ± | ± | — |
| 2 | ± | ± | ± | ± | ± | ± | ± | — |
| 4* | +4 | ± | +2 | ± | +4 | ± | ± | — |
| 6 | +8 | ± | +2 | ± | +8 | ± | +2 | — |
| 8* | +8 | ± | +4 | ± | +16 | ± | +4 | — |
| 10 | +64 | ± | +32 | ± | +32 | ± | +4 | — |
| 12* | +256 | ± | +256 | ± | +128 | ± | +16 | — |
| 14 | +256 | ± | +512 | ± | +256 | ± | +32 | — |
| 16* | +512 | ± | +512 | ± | +512 | ± | +64 | — |
| 18 | +512 | ± | +1024 | ± | +512 | ± | +128 | — |
| 20 | +512 | ± | +1024 | ± | +1024 | ± | +128 | — |

T-O = Primary immunization and pre-immunization blood collection
[1] - Carbohydrates removed
* - Immunization & Booster were made as required in RPMI medium containing 10% fetal calf serum. A suspension of $HIV1_{SF2}$ was harvested from about four-day cultures of CEM in log growth phase, filtered through 0.2 or 0.45 micron filters, aliquoted, and frozen at −70° C. One aliquot was thawed, titrated to determine the $TCID_{50}$, and subsequent assays were performed with freshly thawed aliquots, diluted 1:500 in culture medium to a concentration of approximately ten times the amount required to infect 50% of CEM cells in culture (10 $TCID_{50}$). The virus suspension was mixed with an equal volume (250 ul) of five-fold dilutions of antibody from 1:5 to 1:9,765,625. The virus/antibody mixture was incubated for 60 minutes at 37° C. and duplicate samples of 200 ul used to inoculate wells containing 1.0 ml of approximately $2\times10^5$ CEM cells per well. The cultures were incubated at 37° C. in a humidified, 5% $CO_2$ atmosphere for 14 days. The cells were harvested, pelleted, and lysed with 1% Triton X-100 in PBS for about 10 minutes. The amount of virus (or viral antigen) present in lysed cells was quantitated using a commercially available p24 assay. The titer of neutralizing activity was determined as the reciprocal of the dilution of antibody which inhibited p24 antigen production by greater than 50% of virus control cultures incubated without antibody, or with goat pre-immune IgG prepared in a similar manner. Two hundred microliters of the lysed cellular suspension were assayed.

four HIV wild isolates, including one characterized as a multi-drug resistant strain under conditions identical to those described above. Anti-HIV from the 20 week antibody preparations produced to HIV conjugates devoid of carbohydrate neutralized all strains (Table 8.3B).

Those skilled in the art will recognize that the neutralizing activity produced to HLA-depleted, carbohydrate-depleted HIV proteins is considerably higher than the neutralizing activity typically observed in human anti-HIV sera.

TABLE 8.3B

Analysis of Anti HIV Antibody Neutralization Activity Against Multiple Strains

| HIV Strain/ Isolate | Anti HIV1[1] | Anti HIV2[1] | Anti HIV1 & 2[1] | Pre Immune IgG |
|---|---|---|---|---|
| HIVSF | 10192 | 512 | 20384 | 0 |
| HIVMN | 5096 | 256 | 10192 | 0 |
| Wild#1 | 10192 | 512 | 20384 | 0 |
| Wild#2 | 2048 | 256 | 5096 | 0 |
| Wild#3 | 2048 | 128 | 5096 | 0 |

1 = carbohydrates removed

TABLE 8.3A

Analysis of Anti HIV Antibody Neutralization Activity

| Week # | Group 1 Anti HIV1 | Group 2 Anti HIV1[1] | Group 3 Anti HIV2 | Group 4 Anti HIV2[2] | Group 5 Anti HIV1&2 | Group 6 Anti HIV1&2[1] | Group 7 Anti HIV1&2 | Group 8 Anti HIV1&2 |
|---|---|---|---|---|---|---|---|---|
| T-O* | — | — | — | — | — | — | — | |
| 2 | — | — | — | — | — | — | — | |
| 4* | — | — | — | — | — | 4 | — | — |
| 6 | 32 | 16 | — | — | 16 | 16 | — | — |
| 8* | 256 | 32 | 4 | — | 64 | 128 | 2 | — |
| 10 | 1024 | 128 | 4 | 4 | 512 | 256 | 8 | — |
| 12* | 1024 | 512 | 16 | 8 | 2048 | 1024 | 32 | — |
| 14 | 5096 | 1024 | 256 | 32 | 5096 | 2048 | 64 | — |
| 16* | 10192 | 2048 | 512 | 64 | 10192 | 2048 | 128 | — |
| 18 | 20384 | 2048 | 1024 | 128 | 20384 | 5096 | 128 | — |
| 20** | 20384/204 | 5096/5096 | 2048/256 | 256/256 | 40766/10192 | 10192/10192 | 256/12 | — |

T-O = Primary immunization and pre-immunization blood collection
[1] - Carbohydrates removed
* - Immunization & Booster
** = anti-HIV preparations obtained from the week 20 bleeds were absorbed with human red blood cells and both unabsorbed and absorbed samples were tested under identical conditions. Results are expressed as (unabsorbed/absorbed) neutralization titer.

The anti HIV preparations with the greatest neutralizing activity were produced to HIV-MDP conjugates that were not treated to remove carbohydrate determinants (Table 8.3A). Red blood cell absorption of antibodies to carbohydrate-depleted HIV conjugates had no effect. However, RBC absorption of antibodies to carbohydrate-intact HIV conjugates resulted in a significant reduction in neutralizing reactivity, confirming the presence of phylogenetically present carbohydrate moieties shared between HIV and humans (bottom row, Table 8.3A). All anti-HIV antibody preparations produced to HIV-MDP conjugates were statistically greater than anti-HIV produced using Freund's complete adjuvant. Due to the predicted genetic variability characteristic of HIV, anti-HIV from the 20 week preparations were tested for neutralizing activity using $HIV_{MN}$ and

EXAMPLE 8.4

Effect of Anti HIV on HIV Infected CD4 Lymphocytes in an Antibody Dependent Complement Mediated Cytoxicity Assay Antibodies against carbohydrate-depleted and carbohydrate-intact HIV conjugates were evaluated for complement mediated cytotoxicity reactivity to normal peripheral blood mononuclear cells enriched for CD4 lymphocytes with and without infection with HIV. Normal peripheral mononuclear cells were isolated, subjected to Ficol Hypaque gradient centrifugation and enriched for $CD4^+$ lymphocytes. $CD4^+$ lymphocytes were stimulated with PHA and infected with $HIV_{MN}$ for 7 days in micro culture. Supernatants were removed and replaced with anti HIV produced to HIV preparations following sugar group removal and shown to have no cytotoxic effects on normal cells. As can be seen in Table 8.4, anti HIV lysed infected CD4 lymphocytes in a dose dependent fashion.

was conducted by first attaching a cysteine residue to the resin support. Carbon spacers of various lengths were added; the choice of spacer length varied and was dependent on the

TABLE 8.4

Analysis of Anti HIV Antibody Mediated Cytotoxicity of Infected CD4 Lymphocytes

| Week # | Group 1 Anti HIV1 | Group 2 Anti HIV1[1] | Group 3 Anti HIV2 | Group 4 Anti HIV2[2] | Group 5 Anti HIV1&2 | Group 6 Anti HIV1&2[1] | Group 7 Anti HIV1&2 | Group 8 Anti HIV1&2[1] |
|---|---|---|---|---|---|---|---|---|
| T-O* | ± | ± | ± | ± | ± | ± | ± | — |
| 2    | ± | ± | ± | ± | ± | ± | ± | — |
| 4*   | 4 | 4 | 2 | ± | 4 | 4 | ± | — |
| 6    | 8 | 16 | 2 | ± | 32 | 32 | ± | — |
| 8*   | 32 | 32 | 4 | 4 | 256 | 256 | 2 | — |
| 10   | 128 | 64 | 32 | 32 | 512 | 512 | 8 | — |
| 12*  | 256 | 128 | 256 | 64 | 1024 | 1024 | 16 | — |
| 14   | 1024 | 512 | 512 | 256 | 2048 | 2048 | 16 | 2 |
| 16*  | 2048 | 1024 | 512 | 256 | 4096 | 4096 | 32 | 4 |
| 18   | 4096 | 2048 | 1024 | 512 | 8192 | 8192 | 64 | 8 |
| 20   | 8192 | 4096 | 1024 | 512 | 8192 | 8192 | 256 | 8 |

T-O = Primary immunization and pre-immunization blood collection
[1] - Carbohydrates removed
* - Immunization & Booster

EXAMPLE 8.5

Synthesis of Peptides Corresponding to the Amino Acid Sequence of HIV Proteins

Synthetic peptides were constructed as twelve-mer peptides which mimic the amino acid sequence of $HIV1_{SF2}$. Amino acid sequences for gp 120, gp 41, Vif, gag p 17, gag p 24, nef, Rev, Integrase, Protease, Tat:HxB2 and Reverse Transcriptase and Reverse Transcriptase with overlaps by six amino acid residues were synthesized by and purchased from Purification Systems, Inc. employing solid phase technology.

Butyloxycarbonyl-S-4-methylbenzyl-L-cystine coupled to polystyrene using dicyclohexylcarbodiimide with a catalytic amount of 4-N,N-dimethylaminopyridine was used as the solid-phase support for the synthesis. The amino groups were protected with tert-butyloxycarbonyl (t-BOC) and the side chain protecting groups were as follows: benzyl ether for the hydroxyl of serine, dichlorobenzyl ether for the phenolic hydroxyl of tyrosine, and the beta benzyl-esters were used for the carboxyl groups on glutamic acid and aspartic acid, respectively. Trifluoroacetic acid (40% in $CH_2Cl_2$) was used to remove t-BOC and the resulting salt was neutralized with N-diisopropylethylamine (10% in $CH_2Cl_2$). Diisopropylcarbodiimide was used to couple the t-BOC amino acids. The protecting groups were removed and the peptide was cleaved from the resin at 0° degrees C. with anhydrous hydrogen fluoride containing 10% anisole and 1% ethanedithiol as scavengers. The hydrogen fluoride reagent was removed under vacuum at 0° C. and the peptide then was precipitated and washed with anhydrous ether. After extraction of the peptide from the resin with trifluoroacetic acid, the solvent was evaporated to 15° C. and the peptide was again precipitated with ether. The ether was decanted after centrifugation and the pellet was dissolved in 5% acetic acid with 6 M guanidine HCl. This solution was desalted on a BioGel P2 column equilibrated in 5% acetic acid and the peptide containing fractions were pooled and lyophilized. A cysteine residue was added to the carboxyl terminus of the peptide as needed to provide a functional SH group for the coupling of the peptide to carrier proteins or to a solid support for EIA procedures or to MDP (Example 5). When multiple repeats of the peptide were desired, synthesis was conducted by first attaching a cysteine residue to the resin support. Carbon spacers of various lengths were added; the choice of spacer length varied and was dependent on the application, peptide charge and length and steric influences predicted from preliminary data resulting from peptide attachments to supports. A six carbon spacer such as 6-aminohexanoic acid was first attached with lysine- (lysine) 2-(lysine)4 additions as described above with diaminoethane in Example 5 but altering the sequence of protective group blocking. Amino groups were protected and then deprotected to permit two lysine residues to attach to the deprotected amino terminus, deprotection followed by lysine addition built a branched chain structure for peptide synthesis. Peptides with specific biological function or with sequences that are susceptible to enzymatic degradation were modified by the addition of D-amino acids. One particularly useful addition is the addition of L-alanine-D-isoglutamine with the peptide of interest synthesized off of the $NH_2$ terminus of D-Isoglutamine. In another arrangement, the peptide was synthesized with L-Lysine-L-Lysine-peptide-D-isoglutamine. The carboxy terminal lysine groups are highly susceptible to enzyme degradation by many enzymes in the micro environment while D-isoglutamine both results in an increase in half life of the peptide and provides a hydrophobic site to assemble peptides that require amphipathic properties to elicit a function such as receptor binding and immune induction through MHC associated events. A tyrosine residue was added to the amino terminus for radioactive labeling with $^{125}$Iodine to determine peptide-to-carrier protein coupling efficiency and to identify the peptide during purification. $^{125}$I also provided a tracer to follow the half life of the peptide in biological systems and evaluate receptor binding when peptide function was not affected by tyrosine addition.

EXAMPLE 8.6

The use of Synthetic Peptides Which Mimic Peptide Sequences of HIV and Other Retroviruses, for the Identification of Viral Epitopes Within this invention, synthetic peptide sequences which mimic highly conserved sequences found in HIV and other retroviruses are disclosed and their functional sigificance as immunological targets in treating viral infections are identified. These peptides have further application in the diagnosis and management of HIV infection resulting from HIV microvariants with sequences that contribute to the pathogenesis of HIV through nonspecific down regulation of immune reactions, induction of autoimmunity, and through toxic effects leading to HIV-associated peripheral neuropathy. Each of these events, when presented in a patient, contribute to the pathogenesis of HIV and decline in the quality of life. Synthetic peptides employed to identify and quantitate those HIV-peptide regions which initate those events, have utility in identifying risk factors for autoimmunity and peripheral neuropathy. The synthetic peptides provide further utility in a novel assay procedure to monitor disease progression and changes in progression as a result of treatment.

In one step of this invention, an enzyme immunoassay (EIA) was configured for the identification of goat antibody specificities on HIV not recognized by human anti-HIV. Purified preparations of HIV1 gp120 and gp41 proteins were coated on wells of polyvinyl microtitre plates at 5 ug/ml in phosphate buffered saline (PBS, pH 7.8) by incubation for twenty hours at 37° C. The wells were washed with PBS containing 0.1% Tween 20 (PBS/Tween) and the unoccupied sites of each well were saturated with 5% bovine serum albumin by incubation for 1 hour at 37° C. The plates were used immediately or stored at 4° C. Human IgG anti-HIV (100 ul) (Example 1) was added to each well, incubated for 25 hours at 4° C., and the wells were washed with PBS/Tween. Goat anti-HIV previously produced and labeled with HRP by standard procedures was added to the wells at a dilution required to yield an absorbance of 1.0 in the conditions of the assay (1:10000 titre) and incubated for 24 hours at 4° C. The wells were washed and substrate added to determine amount of binding of the goat IgG. The percent inhibition of binding induced by blocking HIV proteins with human anti-HIV was calculated using the formula.

(OD not blocked-OD blocked)×100—OD blocked negative control/OD not blocked

Minimal blocking of goat anti-HIV-HRP conjugate by human anti-HIV was indicative of binding of goat anti-HIV different from human anti-HIV.

In another step, an EIA was configured to identify epitopes on HIV proteins that were antigenic with goat antibodies but not with human antibodies. Purified preparations of HIV1 gp120 and gp41 proteins were coated on polystyrene beads at 5 ug/ml in PBS by incubation for twenty hours at 37° C. Beads were washed with PBS containing 0.1% Tween 20 (PBS/Tween) and the unoccupied sites on each bead were saturated with 5% bovine serum albumin by incubation for 1 hour at 37° C. Beads were used immediately or stored at 4° C. Human IgG anti-HIV (100 ul) (Example 1) was added to each bead, incubated for 24 hours at 4° C. Human IgG anti-HIV (100 ul) (Example 1) was added to each bead, incubated for 24 hours at 4° C. and the beads were washed with PBS/Tween. Synthetic peptides were dissolved in PBS containing bovine serum albumin (5 mg/ml) and Tween 20 (0.1%) at a concentration of 0.1 mg/ml. The peptides (25 ul) were added to goat anti-HIV IgG-HRP conjugate solution (100 ul) and incubated for 24 hours at 4° C. The mixture then was added to two sets of beads coated with HIV. One set was blocked with human anti-HIV that was added to two sets of beads coated with HIV. One set was blocked with human anti-HIV that was added at the same time as the peptides were added to the goat anti-HIV-HRP conjugate. The beads with reactants were incubated for 24 hours at 4° C. Following incubation, the beads were washed and peroxidase activity was measured as described above. Activity was plotted against peptide position within the HIV proteins. These plots showed areas of the HIV proteins targeted by goat HIV immune IgG that was not recognized by human antibody. When inhibition of binding was observed with a specific synthetic peptide, additional peptides were synthesized to overlap the original peptide by peptides of additional lengths. The lack of inhibition by the synthetic peptides was considered to represent lack of immunologic targeting by the goat immune system. Employing this procedure, linear peptide epitopes were selected for study.

In another preferred procedure of this invention, an EIA was configured to utilize peptide-peroxidase conjugates, produced as disclosed below, to identify antibody reactive epitopes on HIV proteins recognized by the goat but not by the human immune system. Peptides mimicking HIV sequences were covalently attached to HRP to produce an enzyme labeled peptide library for use in mapping antibody specificity. Specifically, HRP was dispensed into a reaction tube at a calculated molar ratio of 1 part HRP:10 parts peptide. Each peptide to be coupled was individually dispensed into microtubes at a concentration of 0.1–1 umole/ml at volumes of 0.1–1 ml, each of which varied dependent upon quantity of conjugate desired and molecular weight of peptide. HRP at a concentration of 1–10 umole/ml was dissolved in 0.1 M carbonate/bicarbonate buffer (pH 9.8) at 4° C. and sodium periodate was added to achieve a final concentration of 0.02 M. The mixture was immediately dispensed into the microtubes containing the peptides mixed and reacted for 30 minutes. Ethylene glycol (0.02 M) was added to quench remaining sodium periodate. The intermediate Schiff's base formed between the amino terminus of the peptide and the aldehyde formed by oxidation of the HRP carbohydrate moieties was reduced by the addition of sodium borohydride (0.2 M) in water. Chromatography of each peptide-peroxidase conjugate in Sephadex G25 was used to remove reactants and excess peptide.

In this preferred assay, the antibody was used to bridge epitopes identified on the HIV proteins prepared from HIV virus lysates and synthetic HIV peptides covalently attached to HRP since antibody reactive with HIV epitopes retained an antigen-binding site which could react with synthetic peptide epitopes attached to peroxidase. Beads were coated with HIV proteins as described above. Coated beads were reacted with goat anti-HIV IgG for 24 hours, the beads were washed and reacted with substrate to determine peroxidase activity and, therefore, peptide binding. With this procedure, only exact epitopes contained within the synthetic peptide were recognized. In this assay, the complete repertoire of goat rectivities was identified. Human anti-HIV and goat anti-HIV reactivities were compared and peptides that reacted only with goat anti-HIV were selected as candidate epitope targets. These data were not considered to be all inclusive of differences between human and goat reactivity to HIV proteins since differences between reactivities and shifts between the amino acid peptide sequence homologies on the HIV protein could result in missing epitope reactivity secondary to the selection of the synthetic peptide.

EXAMPLE 9

Antibody Efficacy as a Therapeutic Agent

A study was conducted with a group of immunochemically designed antibodies to determine the efficacy of the antibodies as a therapeutic agent for the treatment of HIV/AIDS. Specifically, a mixture of lysates of HIV isolates $HIV1_{MN}$, $HIV1_{BAL}$ and $HIV2_{NZ}$, was treated as in Example 3 to remove low molecular weight contaminants and HLA class I and class II antigens and to deglycosylate the HIV proteins. The protein mixture was assayed and found to comprise peptides which mimic the following regions of HIV1$_{SF2}$ proteins:

gp120: an epitope region extending from amino acid residue 4–27 and a second epitope region extending from amino acid residue 54–76;

gp41: an epitope region extending from amino acid residue 502–531;

reverse transcriptase heterodimer p66/55: an epitope region extending from amino acid residue 254–295;

protease p10: an epitope region extending from amino acid region 69–94;

Gag gene protein p24: an epitope region extending from amino acid region 166–181;

Gag gene protein p17: an epitope region extending from amino acid region 2–23 and a second epitope region extending from amino acid region 89–122; and Gage gene protein p7: an epitope region extending from amino acid region 390–41 and 438–443. These amino acid sequences fail to elicit an immune response in humans when contacted through infection or naturally through the environment but do elicit an immune response in other mammalian species.

The purified and treated proteins were enriched and further purified using preparative SDS-PAGE electrophoresis and when desired, by immunoaffinity chromatography employing commercially available (ICN Costa Mesa, Calif. and Advanced Biotechnologies, Columbia, Md.) monoclonal antibodies to gp120, gp41, pp 66/55, p24, p17 and p10 each individually coupled to Sepharose CL4B using procedures known in the art. Following purification, each purified HIV protein peptide of interest was individually conjugated to the MDP microparticle as described in Example 4. HIV-MDP microparticle conjugates were formulated as a cocktail containing equal molar concentrations of each HIV protein/peptide at a final concentration of approximately 1 mg protein/ml in physiological saline. The HIV-MDP cocktail (0.5 ml) was emulsified in squalene (1.5 ml containing 0.05% Tween 80) and injected subcutaneously into 60 goats at 4 to 6 injection sites per goat. Booster immunizations were given at monthly intervals to achieve the desired antibody responses. Monthly serum samples were obtained from each goat preceding the monthly booster and tested by Western Blot analysis, HIV neutralization and enzyme immunoassay disclosed in Example 8.6. Once the desired antibody response was achieved, goats were plasmapheresed from the jugular vein employing a Baxter A 201-A401 Autopheresis machine. The goat red blood cells were returned in physiological saline. The volume of plasma collected from each animal at each plasmapheresis was 350 ml±5.0 ml.

The Caprine immune plasma was fractionated with octanoic acid, after adjustment of the pH to 4.8 with hydrochloric acid. The mixture was centrifuged, filtered and passed through an activated charcoal filter to remove agglomerates and reduce the octanoic acid level to below 0.05%. The immunoglobulin (IgG) containing fraction was further purified by passage through a series of columns:

1. Sephadex G25 with 20 mM phosphate buffer
2. Ion exchange with Whatman DE53 equilibrated in phosphate buffer
3. Sephadex G25 equilibrated in 0.9% saline The final column filtrate was sterile filtered and then either concentrated or diluted to give a final concentration of 10 mg IgG/ml with the desired biological activity. SDS-PAGE and Western Blot analysis demonstrated reactivity of caprine IgG immunoglobulins at a 1:100 dilution with the seven distinct viral proteins as gp120, gp41, p51/66, p24, p17, p7 and p10. Analysis for HIV neutralization demonstrated broad neutralization of HIV1 laboratory and wild strains as disclosed in Example 8.3. Analysis by the enzyme linked immunoassay disclosed in Example 8.3 demonstrated positive reactions to the desired nine epitopes at sample dilutions of 1:1000 or greater. Production lots meeting these criteria were given the trade name of HRG214 as disclosed and consisted of sterile, pyrogen free caprine IgG at a concentration of 10 mg/ml suspended in 0.9% sodium chloride without excipients. Each production lot is compared to the reference lot as disclosed herein to determine equivalence of HRG214 activity. Potency is expressed as mg equivalent/ml.

Males and non pregnant females over the age of 18 were selected based on their having a serodiagnosis of HIV infection documented by Western Blot, with AIDS defining criteria, clinically symptomatic, and with a CD4 T lymphocyte count <300 cells/ul within 30 days prior to study entry. Clinical and laboratory parameters were used to evaluate efficacy. Clinical parameters included changes in opportunistic infections, changes in body weight, changes in gastrointestinal function, including stool consistency and frequency, changes in energy level, changes in appetite, physical strength and endurance, and an overall change in the quality of life. Laboratory parameters included changes in CD4 and CD8 lymphocyte numbers, selected hematology, blood chemistry and urinalysis, and, when available, changes in viral loads by measuring viral RNA by PCR.

The study results showed that with the use of the immunochemically designed antibodies patients improved clinically, with decreases in opportunistic infections, increases in body weight, changes in gastrointestinal function, including less severe diarrhea, increases in energy level, increases in appetite, improvements in physical strength and endurance, and an overall improvement in the quality of life. Laboratory parameters showed improvements, with increases in CD4 and CD8 lymphocyte numbers, improvements in hematology, blood chemistry, and urinalysis numbers, as well as decreases in viral loads by measuring viral RNA by PCR and decreases in infectivity when measured by TCID.

The detailed laboratory results of the study are set forth in the attached Tables 9.1–9.13:

EXAMPLE 9.1

Clinical Evaluation of the Toxicity and Efficacy of HRG214 in Treating HIV-Infected Patients Thirty-five HIV infected patients were treated with HRG214. HRG214 was evaluated for efficacy in reducing HIV viral burden and ameliorating disease progression and symptoms. Patients were stratified by CD4 number/$mm^3$ (<200 and ≧200) and therapeutic regimen:

Group 1: HRG214, CD4<200, n=11;

Group 2: HRG214 and monthly retreatment, CD4<200, n=6;

Group 3: HRG214 and retreatment at progression, CD4<200, n=5;

Group 4: HRG214, CD4>200, n=7;

Group 5: HRG214 and retreatment at progression (patients receiving chemotherapy for malignancy), CD4<200, n=6;

Group 6: Placebo control, CD4>500, n=19;
Group 7: Placebo control, CD4>200–500, n=3.

Patients in treatment groups received 21–28 daily infusions of HRG214 at 1–1.5 mg/kg body weight. Patients with CD4<200 were either retreated x3 days monthly (n=6) or retreated with evidence of HIV progression (n=11). Adverse reactions were limited to minor fever of <2° F., chills, headache, and muscle ache. Clinical chemistry and hematology measurements during and after treatment remained unchanged or improved in all patients over a 90 day period. Twenty-eight patients were evaluated for change in nutritional status. Twenty-four gained 2–22 lbs. body weight with a mean increase of 4.4 lbs. (p=0.0014). Four of the six patients receiving systemic chemotherapy for malignancy remained stable (n=2) or lost weight (2 and 6 lbs respectively). Weight increases correlated directly with increases in serum total protein and albumin measurements. Quantitative HIV-RNA decreased in all treatment groups.

| Group #: Days followed<br>Total = n, Survivor = S | CD4#<br>Pre/Post | CD8#<br>Pre/Post | HIV RNA<br>% Change |
|---|---|---|---|
| Group 1$^{HRG214}$:<br>Day 150, n = 11, S = 4 | 153/156 | 601/699 | −18% |
| Group 2$^{HRG214}$:<br>Day 345, n = 6, S = 6 | 44/168 | 477/1143 | −94% |
| Group 3$^{HRG214+}$:<br>Day 469, n = 5, S = 3 | 25/67 | 705/856 | −67% |
| Group 4$^{HRG214}$:<br>Day 405, n = 7, S = 7 | 315/487 | 970/1164 | −94% |
| Group 5$^{HRG214+}$:<br>Day 469, n = 6, S = 2<br>Chemo | 43/41 | 476/592 | −54% |
| Group 6$^{control}$:<br>Day 469, n = 19 | 909/628 | NA | NA |
| Group 7$^{control}$:<br>Day 469, n = 3 | 315/177 | NA | NA |

The rate of $CD4/mm^3$ loss with time in all treatment groups was reduced (p<0.01) compared to control groups 6 and 7. A sustained CD4 increase was observed in groups 2, 3 and 4. Infectivity measurements by microculture (TCID) demonstrated a 2 log reduction in infectivity by treatment day 7–14 (p<0.001) which was not obvious from quantitative HIV-RNA measurements. Clinical changes included increases in appetite and stamina with marked improvements in chronic fatigue syndrome, diarrhea, malabsorption, candidiasis, CMV (retinitis excluded), Herpes simplex and zoster, cutaneous Molluscum contagiosum, oral hairy leukoplakia, wasting syndrome, bacterial folliculitis and pneumonitis and HIV related peripheral neuropathy were observed.

HRG214 offers a new drug to assist in the management of HIV infection. Data for patient groups 2–5 are presented in more detail below:

Patient Group 2
Patient n=6

Primary Objective: Evaluate safety and efficacy of HRG214 treatment of HIV infection at a daily dose of 1.5 mg/kg/day for 28 days and monthly retreatment x3. Clinical follow-up will continue for 3 years. Patients will have retreat options with recurrence.

End Points: Normalization of clinical and laboratory parameters including improvement in opportunistic infections, incidence of infections, wasting syndrome, peripheral neuropathy and improvement in abnormal blood chemistry and hematology, CD4 and CD8 and reductions in HIV-RNA quantitated by PCR.

Safety variables include: Blood chemistry and hematology and clinical parameters.

Efficacy variable include: HIV-RNA Quantitative by PCR, CD4 and CD8 counts.

Follow up period=3 years
Follow-up period to date=>345 days
Study Demographics: Patient n=6; Start Date—Oct. 23, 1995; As of day 390, Survivors=6; Deaths=0; Lost to follow up=0.
Patient Demographics: HIV positive, AIDS defining criteria with CD4 number <50/mm$^3$.
Treatment Drug(s): HRG-214–1.5 mg/kg/day with monthly retreatments.

TABLE 9.2

Patient Group 2
HIV-RNA QUANTITATIVE BY PCR

| TEST | DAY 1 | DAY 21–28 | DAY 60–90 | DAY 120–150 | DAY 330–390 |
|---|---|---|---|---|---|
| Mean | 4918.3 | 2091.5 | 1338 | 731.8 | 696.6 |
| Std error | 2422.6 | 1222 | 927.2 | 433.1 | 331.2 |
| Maximum | 10649 | 4880 | 3993 | 1825 | 1164 |
| Minimum | 494 | 23 | 19 | 17 | 15 |
| Median | 4265 | 1733.5 | 670 | 542.5 | 466 |

TABLE 9.3

Patient Group 2
QUANTITATIVE CD4/mm$^3$

| TEST | DAY 1 | DAY 21–28 | DAY 60–90 | DAY 120–150 | DAY 330–390 |
|---|---|---|---|---|---|
| Mean | 44 | 52.8 | 52.8 | 109.3 | 167.8 |
| Std error | 14.2 | 19.1 | 16.8 | 33.2 | 41.7 |
| Maximum | 72 | 96 | 82 | 154 | 189 |
| Minimum | 5 | 4 | 5 | 11 | 23 |
| Median | 49.5 | 55.5 | 62 | 136 | 139 |

TABLE 9.4

Patient Group 2
QUANTITATIVE CD8/mm$^3$

| TEST | DAY 1 | DAY 21–28 | DAY 60–90 | DAY 120–150 | DAY 330–390 |
|---|---|---|---|---|---|
| Mean | 477.5 | 437 | 603.3 | 911.8 | 1143 |
| Std error | 157.1 | 171.8 | 173.6 | 228.9 | 286.7 |
| Maximum | 869 | 883 | 804 | 1376 | 1752 |
| Minimum | 145 | 68 | 84 | 319 | 576 |
| Median | 448 | 398.5 | 762.5 | 976 | 1293 |

Patient Group 3
Patient n=5

Primary Objective: Evaluate safety and efficacy of HRG214 treatment of HIV infection at a daily dose of 1.5 mg/kg/day for 28 days. Clinical follow-up will continue for 3 years. Patients will have retreat options with recurrence.

End Points: Normalization of clinical and laboratory parameters including improvement in opportunistic infections, incidence of infections, wasting syndrome, peripheral neuropathy and improvement in abnormal blood chemistry and hematology, CD4 and CD8 and reductions in HIV-RNA quantitated by PCR.

Safety variables include: Blood chemistry and hematology and clinical parameters.

Efficacy variable include: HIV-RNA Quantitative by PCR, CD4 and CD8 counts.

Follow up period=3 year

Follow-up period to date=>469 days

Start date of Jun. 13, 1995; as of day 380, Survivors=3; Deaths=2; Lost to follow up=0

Patient population: HIV positive patients with AIDS defining criteria. Five (5) of the five (5) patients had CD4<50/mm$^3$ blood. HIV-RNA quantitated by PCR demonstrated statistically significant reductions following treatment; day 7 (P=0.0179) and days 21–28 (P=0.043). HIV RNA measurements on days 60–90 and 120–150 demonstrated reduced but increasing HIV RNA values. All 5 patients were retreated (three consecutive doses monthly starting between days 120–150). Following re-treatment a statistically significant (P=0.0006) fall in HIV RNA measurements were observed by Day>250. Statistical analysis was performed using paired t-Test, Wilcoxon Signed Rank Test and Mann-Whitney Rank Sum Test.

START DATE: Jun. 13, 1995

END DATE: Open

TABLE 9.5

Patient Group 2
HIV-RNA QUANTITATIVE BY PCR

| TEST | DAY 1 | DAY 7 | DAY 21–28 | DAY 60–90 | Day 180–210 | Day 240–300 | DAY >380 |
|---|---|---|---|---|---|---|---|
| Mean | 21911 | 10643.2 | 10962.6 | 15231.8 | 18424 | 9385.2 | 8217 |
| Std error | 5003.7 | 3244.3 | 2222.5 | 7385.9 | 5473.5 | 5436.3 | 5135 |
| Maximum | 41182 | 21223 | 17679 | 41922 | 35129 | 30412 | 36412 |
| Minimum | 12292 | 4448 | 3790 | 2984 | 4017 | 1036 | 756 |
| Median | 18976 | 6317 | 11570 | 6787 | 16854 | 4708 | 4926 |

TABLE 9.6

Patient Group 3
QUANTITATIVE CD4/mm$^3$

| TEST | DAY 1 | DAY 7 | DAY 21–28 | DAY 60–90 | Day 180–210 | Day 240–300 | DAY >380 |
|---|---|---|---|---|---|---|---|
| Mean | 25 | 30.8 | 13.8 | 35 | 40.4 | 59.6 | 67 |
| Std error | 6.47 | 8.16 | 3.01 | 9.66 | 13.39 | 25.72 | 33.74 |
| Maximum | 42 | 51 | 20 | 60 | 82 | 154 | 178 |
| Minimum | 9 | 8 | 3 | 10 | 8 | 13 | 16.01 |
| Median | 26 | 24 | 16 | 42 | 28 | 36 | 42.12 |

TABLE 9.7

Patient Group 3
QUANTITATIVE CD8/mm$^3$

| TEST | DAY 1 | DAY 7 | DAY 21–28 | DAY 60–90 | Day 180–210 | Day 240–300 | DAY >380 |
|---|---|---|---|---|---|---|---|
| Mean | 705.6 | 633.6 | 486.4 | 681.4 | 570.8 | 826.6 | 856.24 |
| Std error | 137.8 | 168.2 | 86 | 229 | 120.6 | 200.9 | 226 |

TABLE 9.7-continued

Patient Group 3
QUANTITATIVE CD8/mm$^3$

| TEST | DAY 1 | DAY 7 | DAY 21–28 | DAY 60–90 | Day 180–210 | Day 240–300 | DAY >380 |
|---|---|---|---|---|---|---|---|
| Maximum | 1152 | 1037 | 700 | 1380 | 756 | 1320 | 1346 |
| Minimum | 444 | 220 | 260 | 180 | 101 | 169 | 556 |
| Median | 585 | 828 | 540 | 720 | 638 | 812 | 843 |

Patient Group 4

Patient n=7

Primary Objective: Evaluate toxicity and efficacy of HRG214 treatment of HIV infection at a daily dose of 1.5 mg/kg/day for 28 days with IFN inducer on days 1–7 and 21–23. Clinical follow-up will continue for 3 years. Patients will have retreat options with recurrence.

End Points: Normalization of clinical parameters and laboratory parameters including improvement in OI, incidence of infections, wasting syndrome, etc., in abnormal blood chemistry and hematology, CD4 and CD8, reductions in HIV-RNA quantitated by PCR.

Follow-up period 3 years

Follow-up period to date=>405 days

Study Demographics: Patient n=7; Start Date—Aug. 25, 1995; As of day 390, Survivors=7; Deaths=0; Lost to follow up=0.

Patient Demographics: HIV positive patients with CD4 number>200 without AIDS defining criterion.

Treatment Drug(s): 1.5 mg/kg/day for 28 days. Patients will have retreat options with recurrence.

TABLE 9.8

Patient Group 4
HIV-RNA QUANTITATIVE BY PCR

| TEST | DAY 1 | DAY 21–28 | DAY 60–90 | DAY 180–210 | DAY 330–390 |
|---|---|---|---|---|---|
| Mean | 6078.7 | 964.3 | 899.7 | 658 | 386.2 |
| Std error | 949.4 | 639.6 | 199.1 | 544 | 257 |
| Maximum | 7936 | 2207 | 1257 | 1202 | 983 |
| Minimum | 4808 | 80 | 569 | 114 | 54.1 |
| Median | 5492 | 606 | 873 | 658 | 432 |

TABLE 9.9

Patient Group 4
QUANTITATIVE CD4/mm$^3$

| TEST | DAY 1 | DAY 21–28 | DAY 60–90 | DAY 180–210 | DAY 330–390 |
|---|---|---|---|---|---|
| Mean | 315 | 302.7 | 361.3 | 409.3 | 486.5 |
| Std error | 72.6 | 70.3 | 66.8 | 72.9 | 71.8 |
| Maximum | 429 | 440 | 460 | 540 | 611 |
| Minimum | 180 | 208 | 234 | 288 | 301 |
| Median | 336 | 260 | 390 | 400 | 435 |

TABLE 9.10

Patient Group 4
QUANTITATIVE CD8/mm$^3$

| TEST | DAY 1 | DAY 21–28 | DAY 60–90 | DAY 180–210 | DAY 330–390 |
|---|---|---|---|---|---|
| Mean | 970.7 | 867.7 | 1016 | 1094 | 1164 |
| Std error | 247.7 | 158.7 | 378.8 | 229.5 | 235.2 |
| Maximum | 1464 | 1180 | 1770 | 1550 | 1672 |
| Minimum | 685 | 663 | 576 | 820 | 921 |
| Median | 763 | 760 | 702 | 912 | 986 |

Patient Group 5

Patient n=6

Primary Objective: Evaluate toxicity and efficacy of HRG214 treatment. Clinical follow-up will continue for 3 years. Patients will have retreat options with recurrence.

End Points: Normalization of clinical parameters and laboratory parameters including improvement in OI, incidence of infections, wasting syndrome, etc. in abnormal blood chemistry and hematology, CD4 and CD8, reductions in HIV-RNA quantitated by PCR Follow-up period 3 years Follow-up period to date=>469 days Start date of Jun. 13, 1995; as of day 270, Survivors=2; Deaths=4 (2 deaths between 180–210, 1 death between 240–270; one death after 270); Lost to follow up=0

Patient Population: HIV positive patients with AIDS defining criteria including CD4<200/mm$^3$ blood and disseminated Kaposi's sarcoma. Patients were treated with systemic chemotherapy. Two patients died between days 180–210 and two patients died after day 240. HIV-RNA quantitated by PCR demonstrated reductions at days 60–90, 120–150, 180–210 and 240–270 (p=0.018).

Statistical analysis was performed using paired t Test Wilcox, Signed Rank Test and Mann-Whitney Rank Sum Test.

TABLE 9.11

Patient Group 5
HIV-RNA QUANTITATIVE BY PCR

| TEST | DAY 1 | DAY 21–28 | DAY 60–90 | Day 120–150 | Day 180–210 | DAY 240–270 |
|---|---|---|---|---|---|---|
| Mean | 12483.3 | 16973.7 | 8373.7 | 8237.8 | 8287 | 4717.5 |
| Std error | 3159.1 | 6889.1 | 3081.8 | 2152.3 | 2466.6 | 3609.5 |
| Maximum | 20233 | 46586 | 19514 | 15249 | 15570 | 8327 |
| Minimum | 442 | 1242 | 490 | 1358 | 4708 | 1108 |
| Median | 13682 | 14510 | 7027 | 7392 | 6435 | 4717.5 |

TABLE 9.12

Patient Group 5
QUANTITATIVE CD4/mm$^3$

| TEST | DAY 1 | DAY 21–28 | DAY 60–90 | Day 120–150 | Day 180–210 | DAY 240–270 |
|---|---|---|---|---|---|---|
| Mean | 43.7 | 20.5 | 22.3 | 17.5 | 12.6 | 36 |
| Std error | 31.46 | 12.04 | 8.45 | 6.76 | 4.12 | Undefined |
| Maximum | 200 | 80 | 48 | 48 | 24 | 36 |

TABLE 9.12-continued

Patient Group 5
QUANTITATIVE CD4/mm$^3$

| TEST | DAY 1 | DAY 21–28 | DAY 60–90 | Day 120–150 | Day 180–210 | DAY 240–270 |
|---|---|---|---|---|---|---|
| Minimum | 4 | 4 | 2 | 2 | 4 | 36 |
| Median | 2 | 9.5 | 17 | 11 | 8 | 36 |

TABLE 9.13

Patient Group 5
QUANTITATIVE CD8/mm$^3$

| TEST | DAY 1 | DAY 21–28 | DAY 60–90 | Day 120–150 | Day 180–210 | DAY 240–270 |
|---|---|---|---|---|---|---|
| Mean | 476.3 | 303.5 | 415.8 | 371 | 326.4 | 676 |
| Std error | 152.9 | 62.7 | 1591 | 100.7 | 96.2 | Undefined |
| Maximum | 1170 | 540 | 1152 | 710 | 618 | 676 |
| Minimum | 98 | 86 | 92 | 62 | 101 | 676 |
| Median | 352 | 271.5 | 293.5 | 358 | 245 | 676 |

BIBLIOGRAPHY

1. H. Mitsuya, S. Broder, Nature 325, 773–778 (1987).
2. The Molecular Biology of Tumor Viruses, J. Tooze, et al., Eds. (1973).
3. RNA Tumor Viruses. R. Weiss, Ed. (1982).
4. F. Gonzalez-Scarano, R. E. Shoppe, C. E. Calisher, N. Nathanson, Virology 120, 42–53 (1982).
5. S. Matsuno, S. Inouye, Infection and Immunity 39, 155–158 (1983).
6. J. Mathews, J. Roehrig, The Journal of Immunology 129, 2763–2767 (1982).
7. M. Robert-Guroff, M. Brown, R. Gallo, Nature 316, 72–74 (1985).
8. R. Weiss, et al., Nature 316, 69–72 (1985).
9. T. Matthews, et al., Proceedings of the National Academy of Sciences 83, 9709–9713 (1986).
10. W. Robey, et al., Proceedings of the National Academy of Sciences 83, 7023–7027 (1986).
11. L. Lasky, et al., Science 233, 209–212 (1986).
12. D. Zagury, et al., Nature 326, 249–250 (1987).
13. J. McDougal, et al., Science 231, 382–385 (1986).
14. S. Putney, et al., Science 234, 1392–13905 (1986).
15. S. Norley, R. Kurth, The Retroviridae, J. Levy, Ed. (Plenum Press, 1994), vol. 5.
16. J. Carlson, JAMA 260, 674–679 (1988).
17. J. Lange, et al., British Medical Journal 292, 228–230 (1986).
18. J. McDougal, et al., Journal of Clinical Investigation 80, 316–324 (1987).
19. A. Amadori, A. De Rossi, G. Faulker-Valle, 1. Chieco-Bianchi, Clinical Immunology and Immunopathology 46, 342–351 (1988).
20. A. Amardori, et al., The Journal of Immunology 89, 2146–2152 (1989).
21. E. Barker, S. W. Barnett, L. Stamataos, J. A. Levy, in The Viruses: The Retroviridae J. A. Levy, Ed. (Plenum Press, New York and London, 1995), vol. 4, pp. 1–7.
22. J. A. Levy, in HIV and the Pathogenesis of AIDS A. Press, Ed. (ASM Press, Washington, D.C., 1994) pp. 1–5.

23. D. F. Nixon, K. Broliden, G. Ogg, P.-A. Broliden, *Immunology* 76, 515–534 (1992).
24. P. Linsley, J. Ledbetter, E. Kinney-Thomas, S.-L Hu, *J Virology* 62, 3695–3702 (1988).
25. M. Thali, et al., *J Virology* 66, 5635–5641 (1992).
26. A. Benjouard, J. Gluckmna, H. Rochat, L. Montagnier, E. Bahraoui, *J. Virology* 66, 2473–83 (1992).
27. T. Chanh, et al., *The EMBO Journal* 5, 3065–71 (1986).
28. J. Homsy, M. Meyer, J. Levy, *J. Virology* 64, 1437–40 (1990).
29. M. Tremblay, et al. *J Immunology* 145, 2896–2901 (1990).
30. R. Garry, *Science* 250, 1127–1129 (1990).
31. M. Mackett, G. Smith, B. Moss, *Proc. Natl. Acad. Sci. USA* 79, 7415–7419 (1982).
32. D. Panicali, E. Paoletti, *Proc. Natl. Acad. Sci. USA* 79, 4927–4931 (1982).
33. S.-L. Hu, S. Kosowski, J. Darymple, *Nature* 320, 537–540 (1986).
34. S. Chakrabarti, M. Robert-Guroff, F. Wong-Staal, R. Gallo, B. Moss, *Nature* 320, 535–537 (1986).
35. D. G. Kleid, et al., *Science* 214, 1125–1129 (1981).
36. C. Cabradilla, et al., *Bio/Technology* 4, 128–133 (1986).
37. Current Protocols in *Immunology* (John Wiley & Sons, 1995).
38. *Remington's Pharmaceutical Science* (Mack Publishing Co, Easton, Pa., ed. 15th, 1990).
39. B. Karpovsky, J. Titus, D. Stephany, D. Segal, *Journal of Experimental Medicine* 160, 1686–1701 (1984).
40. P. Cuatrecasas, *Advances in Enzymology* 36, 29 (1972).
41. P. Tijssen, *Practice and Theory of Enzyme Immunoassay* (1985).
42. Stewart, Young, *Solid Phase Peptide Synthesis* (Pierce Chemical Co, ed. 2nd, 1984).
43. J. Tam, et al., *Journal American Chemical Society* 105, 6442 (1983).
44. Maniatis, *Molecular Cloning*: A Laboratory Manual (Cold Spring Harbor Laboratory, 1982).
45. Z. Grabarek, J. Gergely, *Analytical Biochemistry* 185 (1990).
46. J. Staros, R. Wright, D. Swingle, *Analytical Biochemistry* 156, 220–222 (186).
47. R. Timkovich, *Analytical Biochemistry* 79, 135–143 (1977).
48. F. Gelder, et al. *Annals of Surgery*, 591–599 (1991).
49. M. Fung, et al., *J. Virology*, 66, 848–56 (1992)

I claim:

1. An antibody which recognizes and reacts with an epitope which corresponds to or mimics an epitope on a neutralizing or inactivating region of an HIV protein, wherein said neutralizing or inactivating region of said protein fails to elicit an immune response in man when encountered by infection or environmental exposure.

2. An antibody in accordance with claim 1, wherein said epitope has an amino acid sequence which corresponds to or immunologically mimics a portion of a human protein amino acid sequence or a neurotoxin protein amino acid sequence.

3. An antibody in accordance with claim 1, wherein said protein comprises carbohydrate-depleted envelope precursor gp160, gp120 glycoprotein or gp 41 transmembrane glycoprotein.

4. An antibody in accordance with claim 1, wherein said protein comprises a carbohydrate depleted gag precursor p55 or cleaved gag products p17, p24 or p7.

5. An antibody in accordance with claim 1, wherein said protein comprises carbohydrate-depleted protease p10 or reverse transcriptase heterodimer p66/55.

6. An antibody in accordance with claim 2, wherein said human protein comprises alpha fetoprotein, aspartyl protease, deoxyuridine 5'-triphosphate nucleotidohydrolase, eosinophil cationic protein or eosinophil-derived neurotoxin.

7. An antibody in accordance with claim 1, wherein said antibody recognizes an epitope which corresponds to or mimics an epitope on one of the following neutralizing or inactivating regions of HIV isolate $HIV1_{SF2}$:
   (a) a region identified by SEQ ID NO:1;
   (b) a region identified by SEQ ID NO:2;
   (c) a region identified by SEQ ID NO:3;
   (d) a region identified by SEQ ID NO:10;
   (e) a region identified by SEQ ID NO:9;
   (f) a region identified by SEQ ID NO:6;
   (g) a region identified by SEQ ID NOS:7 and 8;
   (h) a region identified by SEQ ID NO:4; or
   (i) a region identified by SEQ ID NO:5.

8. A combination of at least two antibodies, each of which recognizes and reacts with an epitope which corresponds to or mimics an epitope on a neutralizing or inactivating region of an HIV protein, wherein said neutralizing or inactivating region of said protein fails to elicit an immune response in man when encountered by infection or environmental exposure.

9. A combination of antibodies in accordance with claim 8, wherein each of said antibodies recognizes and reacts with an epitope which has an amino acid sequence which corresponds to or immunologically mimics a portion of a human protein amino acid sequence or a neurotoxin protein amino acid sequence.

10. A combination of antibodies in accordance with claim 8, wherein at least one of said antibodies recognizes and reacts with an epitope which corresponds to or mimics an epitope on a neutralizing or inactivating region of carbohydrate-depleted envelope precursor gp160, gp120 glycoprotein or gp 41 transmembrane glycoprotein.

11. A combination of antibodies in accordance with claim 8, wherein at least one of said antibodies recognizes and reacts with an epitope which corresponds to or mimics an epitope on a neutralizing or inactivating region of carbohydrate-depleted gag precursor p55 or cleaved gag products p17, p24 or p7.

12. A combination of antibodies in accordance with claim 8, wherein at least one of said antibodies recognizes and reacts with an epitope which corresponds to or mimics an epitope on a neutralizing or inactivating region of carbohydrate-depleted protease p10 or reverse transcriptase heterodimer p66/55.

13. A combination of antibodies in accordance with claim 9, wherein said human protein comprises alpha fetoprotein, aspartyl protease, deoxyuridine 5'-triphosphate nucleotidohydrolase, eosinophil cationic protein or eosinophil-derived neurotoxin.

14. A combination of antibodies in accordance with claim 8, wherein at least one of said antibodies recognizes an epitope which corresponds to or mimics an epitope on one of the following neutralizing or inactivating regions of HIV isolate $HIV1_{SF2}$:
   (a) a region identified by SEQ ID NO:1;
   (b) a region identified by SEQ ID NO:2;
   (c) a region identified by SEQ ID NO:3;
   (d) a region identified by SEQ ID NO:10;
   (e) a region identified by SEQ ID NO:9;
   (f) a region identified by SEQ ID NO:6;
   (g) a region identified by SEQ ID NOS:7 and 8;
   (h) a region identified as SEQ ID NO:4; or
   (i) a region identified as SEQ ID NO:5.

15. A combination of antibodies in accordance with claim 14, which comprises antibodies which recognize an epitope which corresponds to or mimics an epitope on each of the following neutralizing or inactivating regions of HIV isolate $HIV1_{SF2}$:
   (a) a region identified as SEQ ID NO:1;
   (b) a region identified as SEQ ID NO:2; and
   (c) a region identified as SEQ ID NO:3.

16. A combination of antibodies in accordance with claim 14, which comprises antibodies which recognize an epitope which corresponds to or mimics an epitope on each of the following neutralizing or inactivating regions of HIV isolate $HIV1_{SF2}$:
   (a) a region identified as SEQ ID NO:1;
   (b) a region identified as SEQ ID NO:2;

(c) a region identified as SEQ ID NO:3; and (d) a region identified as SEQ ID NO:9.

17. A combination of antibodies in accordance with claim 14, which comprises antibodies which recognize epitopes which correspond to or mimic epitopes on each of the following neutralizing or inactivating regions of HIV isolate HIV1$_{SF2}$:

(a) a region identified as SEQ ID NO:1;

(b) a region identified as SEQ ID NO:2;

(c) a region identified as SEQ ID NO:3;

and at least one of the following neutralizing or inactivating regions of HIV isolate HIV1$_{SF2}$:

(d) a region identified as SEQ ID NO:9;

(e) a region identified as SEQ ID NO:6;

(f) a region identified as SEQ ID NOS:7 and 8;

(g) a region identified as SEQ ID NO:4; or (h) a region identified as SEQ ID NO:5;

(i) a region identified as SEQ ID NO:10.

18. A combination of antibodies in accordance with claim 8, wherein said antibodies recognize epitopes which corresponds to or mimic epitopes on the following neutralizing or inactivating regions of HIV isolate HIV1$_{SF2}$:

(a) a region identified as SEQ ID NO:1;

(b) a region identified as SEQ ID NO:2;

(c) a region identified as SEQ ID NO:3;

(d) a region identified as SEQ ID NO:10;

(e) a region identified as SEQ ID NO:9;

(f) a region identified as SEQ ID NO:6;

(g) a region identified as SEQ ID NOS:7 and 8;

(h) a region identified as SEQ ID NO:4; and (i) a region identified as SEQ ID NO:5.

19. A composition comprising a combination of antibodies in accordance with claim 14 in a pharmaceutically acceptable carrier.

20. A composition comprising a combination of antibodies in accordance with claim 15 in a pharmaceutically acceptable carrier.

21. A composition comprising a combination of antibodies in accordance with claim 16 in a pharmaceutically acceptable carrier.

22. A composition comprising a combination of antibodies in accordance with claim 17 in a pharmaceutically acceptable carrier.

23. A composition comprising a combination of antibodies in accordance with claim 18 in a pharmaceutically acceptable carrier.

24. An antibody in accordance with claim 1, which is bound to a toxin or a radioactive material.

25. An antibody in accordance with claim 1, which is aggregated with a human T-cell activator.

26. A composition comprising an antibody in accordance with claim 1 in combination with 3'-azido-3'deoxythymidine, 2',3'-dideoxycytidine, 2',3'-dideoxy-2',3'-didehydrocytidine.

27. An antibody which recognizes and reacts with an epitope which corresponds to or mimics an epitope on a neutralizing or inactivating region of a viral protein, wherein said neutralizing or inactivating region of said protein fails to elicit an immune response in man when encountered through infection or the environmental exposure.

28. A combination of at least two antibodies, each of which recognizes and reacts with an epitope which corresponds to or mimics an epitope on a neutralizing or inactivating region of a viral protein, wherein said neutralizing or inactivating region of said protein fails to elicit an immune response in man when encountered through infection or environmental exposure.

* * * * *

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 24 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (v) FRAGMENT TYPE: internal (vi) ORIGINAL SOURCE:
         (A) ORGANISM: Human immunodeficiency virus type 1
         (B) STRAIN: SF2

(xi) SEQUENCE DESCRIPTION: SEQ ID NO:1:

Lys Gly Thr Arg Arg Asn Tyr Gln His Leu Trp Arg Trp Gly Thr Leu
   1               5                  10                  15

Leu Leu Gly Met Leu Met Ile Cys
              20

(2) INFORMATION FOR SEQ ID NO:2:

(i) SEQUENCE CHARACTERISTICS:
         (A) LENGTH: 23 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (v) FRAGMENT TYPE: internal
```

```
      (vi) ORIGINAL SOURCE:
           (A) ORGANISM: Human immunodeficiency virus type 1
           (B) STRAIN: SF2

(xi) SEQUENCE DESCRIPTION: SEQ ID NO:2:

Ala Ser Asp Ala Arg Ala Tyr Asp Thr Glu Val His Asn Val Trp Ala
 1               5                  10                  15

Thr His Ala Cys Val Pro Thr
             20

(2) INFORMATION FOR SEQ ID NO:3:

(i) SEQUENCE CHARACTERISTICS:
           (A) LENGTH: 40 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: Human immunodeficiency virus type 1
           (B) STRAIN: SF2

(xi) SEQUENCE DESCRIPTION: SEQ ID NO:3:

Arg Val Val Gln Arg Glu Lys Arg Ala Val Gly Ile Val Gly Ala Met
 1               5                  10                  15

Phe Leu Gly Phe Leu Gly Ala Ala Gly Ser Thr Met Gly Ala Val Ser
             20                  25                  30

Leu Thr Leu Thr Val Gln Ala Arg
             35                  40

(2) INFORMATION FOR SEQ ID NO:4:

(i) SEQUENCE CHARACTERISTICS:
           (A) LENGTH: 22 amino acids
           (B) TYPE: amino acid
           (C) STRANDEDNESS: Not Relevant
           (D) TOPOLOGY: Not Relevant (ii) MOLECULE TYPE: peptide (iii) HYPOTHETICAL: NO (v) FRAGMENT TYPE: internal (vi) ORIGINAL SOURCE:
           (A) ORGANISM: Human immunodeficiency virus type 1
           (B) STRAIN: SF2

(xi) SEQUENCE DESCRIPTION: SEQ ID NO:4:

Gly Ala Arg Ala Ser Val Leu Ser Gly Gly Glu Leu Asp Arg Trp Glu
 1               5                  10                  15

Lys Ile Arg Leu Arg Pro
             20

(2) INFORMATION FOR SEQ ID NO:5:

(i) SEQUENCE CHARACTERISTICS:
           (A) LENGTH: 28 amino acids
           (B) TYPE: amino acid
           (C) STRANDEDNESS: Not Relevant
           (D) TOPOLOGY: Not Relevant
```

-continued (ii) MOLECULE TYPE: peptide (iii) HYPOTHETICAL: NO (v) FRAGMENT TYPE: internal (vi) ORIGINAL SOURCE:
         (A) ORGANISM: Human immunodeficiency virus type 1
         (B) STRAIN: SF2

(xi) SEQUENCE DESCRIPTION: SEQ ID NO:5:

Leu Tyr Cys Val His Gln Arg Ile Asp Val Lys Asp Thr Lys Glu Ala
1               5                  10                  15

Leu Glu Lys Ile Glu Glu Glu Gln Asn Lys Ser Lys
            20                  25

(2) INFORMATION FOR SEQ ID NO:6:

(i) SEQUENCE CHARACTERISTICS:
         (A) LENGTH: 16 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:6:

Pro Glu Val Ile Pro Met Phe Ser Ala Leu Ser Glu Gly Ala Thr Pro
1               5                  10                  15

(2) INFORMATION FOR SEQ ID NO:7:

(i) SEQUENCE CHARACTERISTICS:
         (A) LENGTH: 21 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:7:

Lys Thr Val Lys Cys Phe Asn Cys Gly Lys Glu Gly His Ile Ala Lys
1               5                  10                  15

Asn Cys Arg Ala Pro
            20

(2) INFORMATION FOR SEQ ID NO:8:

(i) SEQUENCE CHARACTERISTICS:
         (A) LENGTH: 6 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (v) FRAGMENT TYPE: internal (vi) ORIGINAL SOURCE:
         (A) ORGANISM: Human immunodeficiency virus type 1

(xi) SEQUENCE DESCRIPTION: SEQ ID NO:8:

Lys Ile Trp Ser Ser Gln
1               5

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: Human immunodeficiency virus type 1

(xi) SEQUENCE DESCRIPTION: SEQ ID NO:9:

Arg Ile Gly Gly Gln Leu Lys Glu Ala Leu Leu Asp Thr Gly Ala Asp
1               5                   10                  15

Asp Thr Val Leu Glu Glu Met Asn Leu Pro
            20                  25

(2) INFORMATION FOR SEQ ID NO:10:

(i) SEQUENCE CHARACTERISTICS:
        (A) LENGTH: 42 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: Human immunodeficiency virus type 1

(xi) SEQUENCE DESCRIPTION: SEQ ID NO:10:

Gly Leu Lys Lys Lys Lys Ser Val Thr Val Leu Asp Val Gly Asp Ala
1               5                   10                  15

Tyr Phe Ser Val Pro Leu Asp Lys Asp Phe Arg Lys Tyr Thr Ala Phe
            20                  25                  30

Thr Ile Pro Ser Ile Asn Asn Glu Thr Pro
            35                  40

(2) INFORMATION FOR SEQ ID NO:11:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: Human immunodeficiency virus type 2
        (B) STRAIN: NZ (xi) SEQUENCE DESCRIPTION: SEQ ID NO:11:

Gln Leu Leu Ile Ala Ile Val Leu Ala Ser Ala Tyr Leu Ile His Cys
1               5                   10                  15

Lys Gln Phe Val Thr Val Phe Tyr Gly Ile Pro Ala Trp Arg Asn Ala
            20                  25                  30

Ser Ile Pro Leu Phe
            35

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: Human immunodeficiency virus type 1
        (B) STRAIN: SF2

(xi) SEQUENCE DESCRIPTION: SEQ ID NO:12:

Gly Ile Val Gly Ala Met Phe Leu Gly Phe Leu Gly Ala Ala Gly Ser
1               5                   10                  15

Thr Met Gly Ala
            20

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal (vi) ORIGINAL SOURCE:
        (A) ORGANISM: Human immunodeficiency virus type 1
        (B) STRAIN: SF2

(xi) SEQUENCE DESCRIPTION: SEQ ID NO:13:

Phe Leu Gly Phe Leu Gly Ala Ala Gly Ser
1               5                   10

(2) INFORMATION FOR SEQ ID NO:14:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (v) FRAGMENT TYPE: internal

```
       -continued (vi) ORIGINAL SOURCE:
     (A) ORGANISM: Human immunodeficiency virus type 2
     (B) STRAIN: NZ (xi) SEQUENCE DESCRIPTION: SEQ ID NO:14:

Leu Leu Ile Ala Ile Val Leu Ala Ser Ala Tyr Leu Ile His Cys Lys
1               5                   10                  15

Gln
```